(12) United States Patent
Müller et al.

(10) Patent No.: US 8,057,041 B2
(45) Date of Patent: Nov. 15, 2011

(54) APPARATUS FOR MEASURING AN ANALYTE IN AN EYE FLUID

(75) Inventors: Achim Müller, Grossostheim (DE); Peter Herbrechtsmeier, Königstein (DE); Klaus Haberstroh, Bodman-Ludwigshafen (DE); Roman Gruler, Rottweil (DE)

(73) Assignee: EyeSense AG, Basel (CH)

( * ) Notice: Subject to any disclaimer, the term of this patent is extended or adjusted under 35 U.S.C. 154(b) by 88 days.

(21) Appl. No.: 12/374,772

(22) PCT Filed: Jul. 23, 2007

(86) PCT No.: PCT/EP2007/057581
§ 371 (c)(1),
(2), (4) Date: Nov. 6, 2009

(87) PCT Pub. No.: WO2008/012288
PCT Pub. Date: Jan. 31, 2008

(65) Prior Publication Data
US 2010/0053556 A1     Mar. 4, 2010

(30) Foreign Application Priority Data
Jul. 24, 2006   (EP) ..................................... 06015332

(51) Int. Cl.
*A61B 3/00*      (2006.01)
*A61B 3/10*      (2006.01)
(52) U.S. Cl. .......................... 351/219; 351/205; 351/247
(58) Field of Classification Search .................. 351/219, 351/200, 205, 246–247
See application file for complete search history.

(56) References Cited

U.S. PATENT DOCUMENTS
3,122,472 A    2/1964   Waritz
(Continued)

FOREIGN PATENT DOCUMENTS
| | | |
|---|---|---|
| EP | 0 868 881 B1 | 10/1998 |
| GB | 2 409 033 A | 6/2005 |
| WO | WO 01/13783 A1 | 3/2001 |
| WO | WO 02/087429 A1 | 11/2002 |
| WO | WO 2004/071287 A1 | 8/2004 |

OTHER PUBLICATIONS
International Preliminary Report on Patentability (Translation) for related International Patent Application No. PCT/EP2007/057581 dated Nov. 14, 2008.

*Primary Examiner* — Dawayne Pinkney
(74) *Attorney, Agent, or Firm* — Fanelli Haag PLLC

(57) ABSTRACT

The invention proposes a manual measuring appliance (112) and an analytical measuring system (110) which can be used to measure at least one analyte in an eye fluid of an eye (114). The handheld measuring appliance (112) comprises a measuring system (120) and a positioning system (122). The measuring system (120) can measure at least one property of the at least one analyte and/or at least one analyte-dependent change of property of at least one ocular sensor (116) in the eye fluid, and this can be used to infer a concentration of the analyte in the eye fluid. The positioning system (122) is set up to measure a spatial positioning, wherein the spatial positioning comprises a distance between at least one measurement location in the eye (114) and the handheld measuring appliance (112) and also furthermore at least one further positioning co-ordinate. The positioning system (122) comprises at least one of the following systems: a camera system, particularly a monocular or binocular camera system, having at least one camera (410; 910); an image recognition system; a triangulation system; a propagation time measuring system, particularly for 1-, 2- or 3-dimensional propagation time measurement, particularly using at least one laser and/or at least one phase mix detector (PMD); a 1-, 2- or 3-dimensional intensity measuring system for at least one signal; a 2- or 3-dimensional magnetoresistive measuring system.

30 Claims, 16 Drawing Sheets

U.S. PATENT DOCUMENTS

| | | |
|---|---|---|
| 6,122,042 A | 9/2000 | Wunderman et al. |
| 2003/0086073 A1 | 5/2003 | Braig et al. |
| 2004/0138539 A1 | 7/2004 | Jay et al. |
| 2005/0121322 A1 | 6/2005 | Say et al. |
| 2006/0239670 A1* | 10/2006 | Cleveland ........................ 396/51 |
| 2006/0247765 A1* | 11/2006 | Fedor ........................... 623/6.11 |
| 2007/0002470 A1* | 1/2007 | Domschke et al. ........... 359/819 |
| 2010/0331634 A1* | 12/2010 | Muller et al. ................. 600/309 |

* cited by examiner

APPARATUS FOR MEASURING AN ANALYTE IN AN EYE FLUID

FIELD OF THE INVENTION

The invention relates to a handheld measuring appliance for measuring at least one analyte in an eye fluid and to an analytical measuring system which contains the handheld measuring appliance according to the invention. The invention also relates to a method for determining a concentration of at least one analyte in a body fluid which uses the analytical measuring system. Such handheld measuring appliances, analytical measuring systems and methods are used for determining blood sugar concentration, for example.

PRIOR ART

Determining blood sugar concentration and appropriate medication is an essential part of the daily sequence for diabetics. In this case, the blood sugar concentration needs to be determined quickly and easily several times per day, typically 2-7 times, in order to be able to take appropriate medical measures where necessary. In many cases, the medication is provided by means of automatic systems, particularly using insulin pumps.

Conventional systems for determining blood sugar concentration are normally based on the patient or a doctor perforating an area of skin, for example using a suitable lancet system, and thereby generating a blood sample. This sample is then analyzed for its blood sugar content using suitable measuring methods, for example optical and/or electrochemical measuring methods.

To reduce the hardships associated with frequent generation of blood samples for the patients, various noninvasive or minimally invasive technologies for measuring blood sugar concentrations have been developed. One technology is based on the measurement of glucose in eye fluids, such as tear fluid, aqueous humor or interstitial fluid. By way of example, WO 01/13783 describes an ocular sensor for glucose which is in the form of an eye lens. The ocular sensor comprises a glucose receptor, which is marked with a first fluorescence label, and a glucose competitor, which is marked with a second fluorescence label ("Donor"). The two fluorescence labels are selected such that when the competitor is bound to the receptor, the fluorescence of the second fluorescence label is quenched on account of a resonant fluorescence energy transfer. By monitoring the alteration in the fluorescence intensity at a wavelength around the fluorescence maximum of the quenchable fluorescence label, it is possible to measure the proportion of the fluorescence-marked competitor which has been displaced by the glucose. In this way, the glucose concentration in the eye fluid can be determined. This measurement can in turn be used to infer the blood sugar concentration therefrom. Other types of evidence are also conceivable and familiar to a person skilled in the art, for example fluorescence evidence for the first fluorescence label.

WO 02/087429 also describes a fluorescence photometer which can be used to determine blood sugar concentrations by measuring the glucose concentration in an eye fluid. The apparatus shown is capable of simultaneously measuring two fluorescence intensities for a donor at two different wavelengths.

The measurement of glucose or other analytes in eye fluids is usually limited by various factors. An example of one factor is that the eye fluids are usually available only in small quantities (such as tear or interstitial fluids) or can be accessed only with difficulty (vitreous humor or aqueous humor). Hence, the opportunity for collecting these eye fluids as a sample is usually a very difficult procedure. To get around or reduce this restriction or difficulty, various options for in-vivo measurement have been developed. The aforementioned WO 01/13783 shows an in-vivo measuring system of this type.

One difficulty of these in-vivo measuring systems, however, is that in many cases exact positioning of the measuring appliance relative to the eye or relative to the eye lens used is a critical prerequisite on which the accuracy of the measurement is crucially dependent.

Therefore, WO 2004/071287 shows a fluorescence photometer which uses two different beams and allows correct positioning of the measuring appliance in front of the eye. A pilot beam is used to excite a first fluorescence in the pupil, and this is used to ascertain a distance between the fluorescence photometer and the eye. When a correct interval is set, a measuring beam is automatically started which excites a second fluorescence in the analyte sensor in the eye, which can in turn be used to determine the analyte concentration.

Despite the considerable measurement complexity with which the system shown in WO 2004/071287 is associated, it has been found that measuring the analyte concentration continues to be subject to large variations. In addition, positioning operations performed independently by the patient are required in many cases and can be performed only with difficulty, particularly by older patients or children.

U.S. Pat. No. 3,1220,472 discloses an apparatus for the photometric analysis and/or identification of properties of an object. The apparatus comprises a plurality of light sources with prescribed light sources which are actuated in a chronological sequence. In addition, a plurality of physically separate light detectors is provided which detect radiation emitted by the object. Inter alia, a leg construction with moving legs is also provided which can be used to measure a distance between the apparatus and the surface of the object and can be used to perform coarse angle measurement.

The apparatus disclosed in U.S. Pat. No. 3,1220,472 is not suitable for the fluorescence photometric determinations of glucose concentration in an eye fluid, however, for various reasons. One drawback is particularly that the leg construction is barely able to be placed on the sensitive surface of the eye by a patient. If the leg construction is placed on the surface of the forehead in the region of the eye sockets, on the other hand, movement of the eye immediately results in a marked change in the position of the object to be measured (e.g. the pupil) relative to the measuring apparatus. These deviations corrupt the positioning such that the position information becomes essentially unusable for the high precision fluorescence photometric measurements. A further difficulty is that the coarse angle measurement using the leg construction already has the inherent trouble of a high level of uncertainty, which usually cannot be tolerated for biomedical precision measurements.

OBJECT OF THE INVENTION

It is therefore an object of the present invention to provide an apparatus which can be used to determine the concentration of the analyte in the eye fluid reliably, quickly and easily, the intention being to avoid the drawbacks described for the apparatuses which are known from the prior art.

DESCRIPTION OF THE INVENTION

This object is achieved by the invention with the features of the independent claims. Advantageous developments of the invention are characterized in the subclaims. The wording of all the claims is hereby made the content of this description by way of reference.

The invention is essentially based on the insight that the reproducibility of the measurement is dependent not only, as described in WO 2004/071287, for example, on the distance of a measuring appliance from the eye, but also in many cases on an angular position of the measuring appliance relative to the viewing direction and/or on an angular orientation of the measuring appliance (rotation, tilting) relative to the eye. A concept on which the invention is based is therefore that of combining known ophthalmic diagnostic measuring appliances for determining analyte concentration with position finding and/or positioning systems which are to date known only from the field of process automation or robotics.

Accordingly, a handheld measuring appliance for measuring at least one analyte in an eye fluid of an eye is proposed which comprises a measuring system and a positioning system. By way of example, the eye fluids may be the fluids described at the outset. The at least one analyte may be glucose and/or a hormone or else other types of analytes, for example.

The measuring system and the positioning system are defined functionally in this case, which means that these systems do not necessarily need to be separate systems. Individual functions of these systems can also be performed wholly or in part by the same components or else wholly or in part by a computer, for example a microcomputer which has been set up by programming (e.g. using appropriate software modules), at the same time.

The measuring system is set up to measure at least one property of the analyte itself and/or at least one analyte-dependent property change in at least one ocular sensor in the eye fluid. The positioning system is set up to measure a spatial positioning.

In contrast to the prior art, this spatial positioning, in line with the invention, comprises not only a simple distance between at least one measurement location in the eye and the handheld measuring appliance but also at least one further positioning co-ordinate. This at least one further positioning co-ordinate preferably comprises at least one of the following variables: an angle from a virtual connecting line between the handheld measuring appliance and the at least one measurement location in a prescribed angle system (for example relative to a viewing direction of the eye), a (e.g. Cartesian) co-ordinate of the handheld measuring appliance, a (e.g. Cartesian) co-ordinate of the at least one measurement location and/or an orientation angle (rotation, tilting) of the handheld measuring appliance in a prescribed co-ordinate system.

For the way in which the measuring system works, it is possible to refer to the documents cited at the outset, for example. The measuring system is set up to react to the analyte itself (for example a fluorescence for glucose) or, alternatively or in addition, indirectly to the presence of the analyte using an ocular sensor in the eye fluid. Besides the systems known from the prior art, however, other measuring systems are also proposed. Thus, the measuring system preferably comprises at least one of the following systems: an infrared (IR) spectroscopic measuring system, a near infrared (NIR) spectroscopic measuring system, a RAMAN spectroscopic measuring system, a UV/visible (UV/VIS) spectroscopic measuring system, a fluorescence measuring system, an impedance measuring system, a photoacoustic measuring system, a circular dichroic measuring system, a refractometric measuring system, an interferometric measuring system. Such measuring systems and the design thereof are known to a person skilled in the art from other areas of technology.

For the positioning system, various contactless precision techniques have been developed and tested which allow simple and reliable measurement of the positioning down to the micron range. Thus, the positioning system comprises at least one of the following systems: a camera system, particularly a monocular or binocular camera system, having at least one camera; an image recognition system; a triangulation system; a propagation time measuring system, particularly for 1-, 2- or 3-dimensional propagation time measurement, particularly using at least one laser and/or at least one phase mix detector (PMD); a 1-, 2- or 3-dimensional intensity measuring system for at least one signal; a 2- or 3-dimensional magnetoresistive measuring system. In addition, the positioning system may additionally comprise a measuring system for comparing at least two signals measured by means of two sensors in a different spatial arrangement.

By way of example, the handheld measuring appliance may be set up such that the positioning system automatically triggers a measurement by the measuring system when at least one prescribed nominal positioning or a prescribed nominal positioning range (for example a tolerance range) is reached. Alternatively or in addition, the handheld measuring appliance may also be set up such that, under the control of the positioning system, a spatial position and/or spatial orientation of the measuring system is actively set. By way of example, this can be done such that as soon as the handheld measuring appliance is positioned within a prescribed tolerance range on the basis of the information provided by the positioning system, the spatial position and/or spatial orientation of the measuring system within the handheld measuring appliance is set further by controllable actuating elements, for example electromechanical actuating elements, particularly a piezo controller. As a further possibility which may be used alternatively or in addition, the handheld measuring appliance and particularly the positioning system are preferably set up such that a feedback signal can be generated for a user and provides information about the spatial positioning. By way of example, this can be done by means of a display or other optical signals or else by means of acoustic signals. Optical signals may contain advice for the user regarding the direction in which the handheld measuring appliance needs to be moved and/or rotated/tilted for optimum positioning, for example. This advice may be provided by means of appropriate arrows or in written form, for example.

As described at the outset, the handheld measuring appliance is preferably set up not only to determine the concentration of the at least one analyte in the eye fluid but preferably also to determine the analyte concentration in another body fluid, particularly in blood or tissue fluid. This determination of concentration can be effected taking account of the information provided by the positioning system, for example. Thus, the ascertained analyte concentration can be corrected from a known angle, distance and/or position dependency of the signal picked up by the measuring system (for example a fluorescence signal) using the known positioning, for example.

To further increase the accuracy of the measurement, it is additionally possible for a calibration system to be provided which is set up to perform a comparison measurement of at least one analyte concentration in a body fluid and/or to adopt measurement data from an appropriate comparison measurement performed using a separate measuring appliance. The results of this comparison measurement or the comparison measurement data are then taken into account when determining the concentration of the at least one analyte using the handheld measuring appliance. By way of example, the calibration system may comprise a commercially available system which determines for example a blood sugar concentration using a customary electrochemical (for example amperometrically with glucose oxidase or glucose dehydrogenase or hexokinase) or optically (for example using photometric measuring strips). This calibration system can be integrated into the handheld measuring appliance, and the measurement result can be transferred directly to the algorithm for determining the glucose concentration.

The idea of the integrated calibration system can also be used independently of the proposed handheld measuring appliance. Thus, by way of example, a measuring system which is set up to measure at least one property of the at least one analyte and/or at least one analyte-dependent property change in at least one ocular sensor in the eye fluid can be combined with a calibration system in one of the embodiments described above. The measuring system may in this case correspond to one of the embodiments illustrated in this description. This integration can be effected regardless of whether or not a positioning system is still provided. This provides a convenient way of comparing and calibrating an "indirect" measurement of the at least one analyte in the eye fluid, or following appropriate conversion also in another body fluid, with a "conventional" measurement (for example an electrochemical blood sugar measurement, etc.). The calibration system and measurement system can conveniently be integrated in a single appliance (e.g. with a common housing). Complex data interchange, which is susceptible to errors, between two appliances (a separate calibration appliance and the measuring system), which would need to be effected manually or through the interchange of signals, for example, is therefore not necessary. Advantageously, it is possible to use common operator control and display elements and common computer resources and memory elements. By way of example, the integrated appliance can also ask the patient (for example at regular intervals, after the occurrence of a fault or after a system change) to perform a calibration measurement and can use the calibration data obtained in this manner automatically, for example, to convert the measurement data obtained using the measuring system, for example directly into a concentration of the at least one analyte in another body fluid (e.g. glucose concentration in blood). This integration is therefore extremely user friendly and insensitive to interference overall.

Besides the handheld measuring appliance, the invention also proposes an analytical measuring system for measuring the at least one analyte in the eye fluid. The analytical measuring system comprises a handheld measuring appliance based on one of the embodiments described above and also at least one ocular sensor. The at least one ocular sensor is suitable for being placed in contact with the eye fluid. Accordingly, the at least one ocular sensor may have an eye lens, particularly a contact lens and/or an eye implant, for example. The at least one ocular sensor is designed to change at least one property upon contact with the at least one analyte, the at least one change of property being able to be measured using the measuring system of the handheld measuring appliance. In particular, the at least one ocular sensor may have, in a similar fashion to the prior art described at the outset, at least one analyte receptor with at least one first fluorescence label and at least one analyte competitor with at least one second fluorescence label (subsequently also called "donor"). In this case, the at least one analyte receptor and the at least one analyte competitor are intended to be in a form such that at least one property of the ocular sensor, particularly at least one fluorescence property, changes when the at least one analyte competitor is bound to the at least one analyte receptor. In addition, the at least one ocular sensor may advantageously also have one or more reference fluorophors and/or reference colorants (subsequently also called simply "reference"), which do not change their properties when the at least one analyte is present. This at least one reference fluorophor and/or reference colorant can be used by the positioning system for analyte-independent measurement of the spatial positioning, for example (see also the exemplary embodiments shown below).

As an alternative or in addition, the at least one ocular sensor may also have at least one grating and/or at least one hologram, which are respectively designed to change at least one reflection property upon contact with the at least one analyte. By way of example, a Bragg grating can be used. From the change in the at least one reflection property, for example the change in the Bragg angle, the measuring system can infer the presence and/or the concentration of the at least one analyte.

To further improve the measurement of the spatial positioning by the positioning system and hence to further increase the accuracy of the analytical measuring system, the analytical measuring system may also additionally comprise at least one positioning sensor. This at least one positioning sensor may be separate from the at least one ocular sensor (for example likewise accommodated in the eye) or may be part of the at least one ocular sensor. By way of example, the at least one positioning sensor may have an eye lens, particularly a contact lens and/or an eye implant, or may be part of one of these elements.

The at least one positioning sensor is intended to be designed to generate at least one signal which can be detected by the positioning system. This at least one detectable signal may be a shape (for example an outline) which can be detected by the positioning system or may be a marker. As an alternative or in addition, this signal may also be a fluorescence signal, a magnetization, a reference fluorescence signal and/or a reference color signal. Changes in these signals can also be advantageously sensed by the positioning system. Combinations of said signal types are also conceivable, for example a combination comprising an outline (e.g. a form which can be recognized by an image recognition system) and a color signal.

The handheld measuring appliance described and the analytical measuring system described can be used in various ways. A preferred method for determining a concentration of at least one analyte (for example glucose) in a body fluid (for example blood) using the described analytical measuring system in one of the illustrated embodiments has the method steps presented below. In this case, the method steps shown do not necessarily need to be carried out exactly in the order shown, and it is also possible for additional method steps which are not shown to be carried out. It is also possible for individual method steps or a plurality of method steps to be carried out wholly or partially in parallel with one another or repeatedly.

First of all, the handheld measuring appliance is positioned coarsely in front of the eye on which measurements are to be taken. Next, the spatial positioning is determined and a measurement by the measuring system is triggered. These method steps may be in different forms, as described above, for example by virtue of the spatial positioning measured (which may also be a repeated measurement) being used for evaluating the measurement by the measuring system, positioning of the handheld measuring appliance being influenced and/or the measuring system being finely positioned automatically.

Next, the concentration of the at least one analyte in the eye fluid is determined from the at least one measured property of the at least one analyte and/or the at least one measured change of property of the at least one ocular sensor. From this analyte concentration in the eye fluid, a known relation, for example stored in a data store, is then used to infer the concentration of the at least one analyte in the body fluid.

Further method steps may comprise, by way of example, storage of the data, presentation of the measurement values on a display element (for example a display), warning functions (for example when prescribed limit values are exceeded), control of medication appliances (for example an insulin pump), graphical data preparation, database functions and/or data interchange with other appliances (for example an insulin pump and/or a separate computer). Other functions are possible.

In addition, as described above, the analytical measuring system and particularly the handheld measuring appliance preferably comprise various computer functions which can be implemented by a microcomputer with the relevant inward and outward appliances, storage media and the like, for example. Accordingly, the invention also proposes a computer program with program code which can be stored particularly on a machine-readable medium, the computer program being suitable for supporting the described method steps of the method according to the invention wholly or in part upon execution on a computer or computer network. In particular, the method steps of spatial position finding, triggering the measurement, determining the concentration of the at least one analyte in the eye fluid and/or determining the concentration of the at least one analyte in the body fluid can be implemented wholly or in part by means of an appropriate computer program.

Further details and features of the invention can be found in the description below of preferred exemplary embodiments in conjunction with the subclaims. In this case, the respective features may be implemented separately on their own or in multiples in combination with one another. The invention is not limited to the exemplary embodiments.

The exemplary embodiments are shown schematically in the figures. Identical reference numerals in the individual figures denote elements which are the same or have the same function or correspond to one another in terms of their functions.

Specifically:

Figure 1:
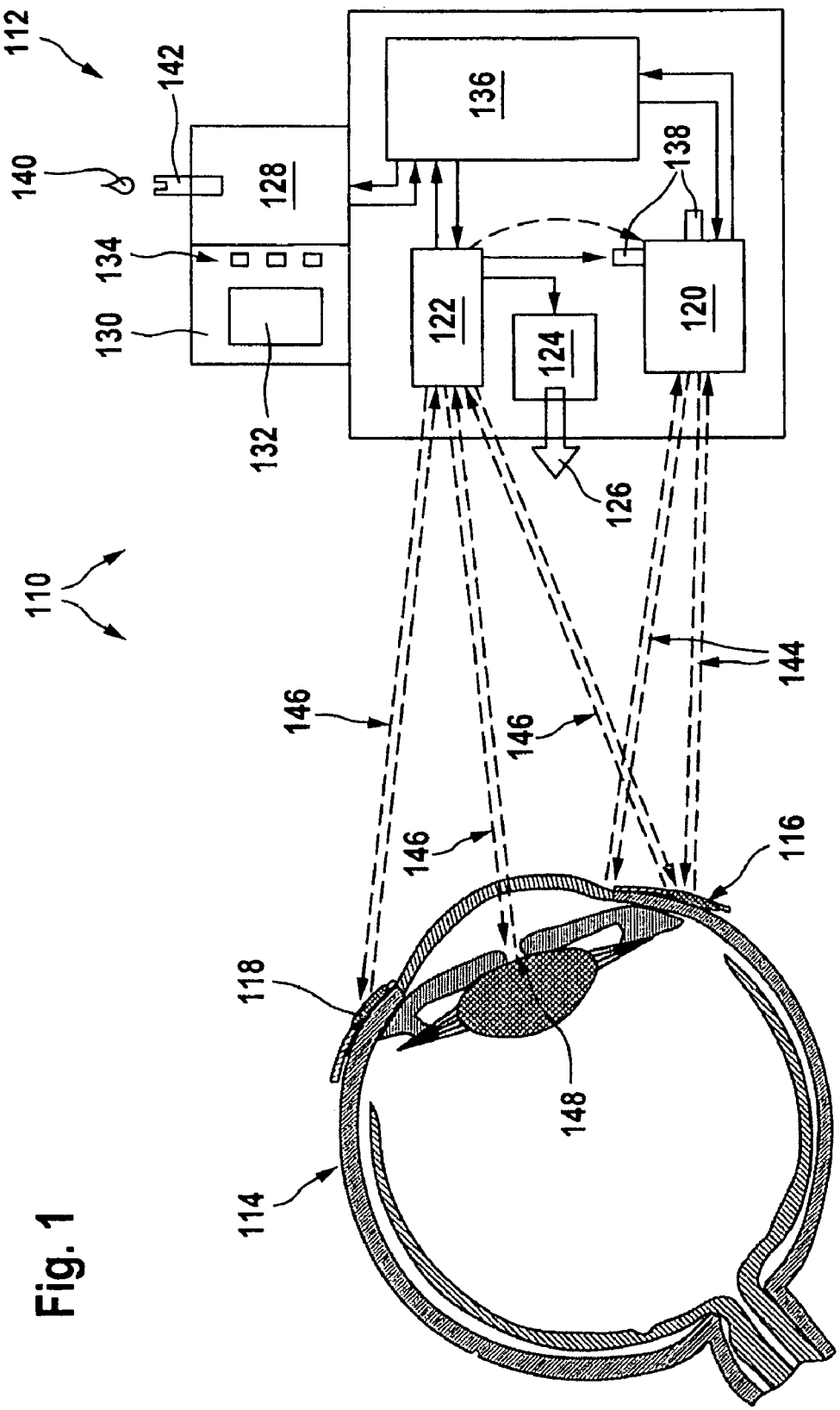
FIG. 1 shows an analytical measuring system with a handheld measuring appliance for measuring at least one analyte.

FIG. 1 shows a schematic basic illustration of an analytical measuring system 110 according to the invention, which is intended to be used to explain individual components and the operation thereof below. The analytical measuring system 110 comprises a handheld measuring appliance 112 and also an ocular sensor 116, accommodated in or on one eye 114, and a positioning sensor 118. As explained above, the ocular sensor 116 and the positioning sensor 118 are optional, since the handheld measuring appliance 112 can also perform a measurement using an intrinsic fluorescence of the analyte which is to be demonstrated, for example, and since the positioning measurement can also be made, in principle, without a positioning sensor 118. In addition, the functions of the ocular sensor 116 and the positioning sensor 118 could also be adopted by a common component.

As fundamental components, the handheld measuring appliance 112 comprises a measuring system 120 and a positioning system 122. In addition, this schematic exemplary embodiment contains a feedback unit 124 for generating a feedback signal 126, a calibration system 128, an operator control unit 130 with visual display elements 132 (for example one or more displays) and operator control elements 134 (for example keys, switches, etc.) and also a central computation unit 136 (for example a microcomputer with one or more volatile and/or nonvolatile data stores). The individual components cited are preferably connected to one another (shown by arrows in FIG. 1 symbolically and without any claim to completeness), which means that, by way of example, it is possible for the feedback unit 124 and/or the measuring system 120 to be controlled by the positioning system 122 (directly or indirectly, for example via the central computation unit 136).

In addition, the exemplary embodiment of the handheld measuring appliance 112 contains a piezo controller 138 for setting the spatial position and/or the spatial orientation of the measuring system 120. The positioning system 122 influences (indicated by the dashed arrow) this piezo controller 138 directly or indirectly via the central computation unit 136.

In the example in FIG. 1, it will be assumed that the at least one analyte to be demonstrated is glucose. Accordingly, the calibration system 128 is equipped to perform a "conventional" comparison measurement of a glucose concentration. This is illustrated symbolically in FIG. 1 by a drop of blood 140 and a test strip 142 (for example electrochemical or optical), the test strip 142 being able to be read by the calibration system 128. A person skilled in the art is also familiar with other possible embodiments of the calibration system 128.

In addition, FIG. 1 symbolically shows the manner of measurement of the measuring system 120 and also of the positioning system 122, in each case by straight, dashed concentrations of arrows from the handheld measuring appliance 112 to the eye 114. However, it should be pointed out that these concentrations of beams do not lay claim to completeness, since, as illustrated above, various principles can be used both for the positioning system 122 and for the measuring system 120. Also, there need not necessarily be bidirectionality of the measurements, as illustrated symbolically by double arrows in FIG. 1, but rather it is also possible for signals to be transmitted merely from the eye 114 to the handheld measuring appliance 112, for example, without there being any excitation by the handheld measuring appliance 112.

As illustrated above, the measurement of the glucose concentration in the eye fluid of the eye 114 which is performed by the measuring system 120 is based either on direct measurement of a property of the glucose (for example a fluorescence property) or, alternatively or in addition, on at least one analyte-dependent property change in the ocular sensor 116, for example a change in a fluorescence property of the ocular sensor 116 in line with the glucose concentration. Accordingly, in FIG. 1 the "measurement signals" 144 run symbolically between the measuring system 120 and the ocular sensor 116 and/or other regions of the eye 114. In line with the measuring method used, the measurement signals 144 may comprise, by way of example, one or more (i.e. a plurality of wavelengths, for example) excitation beams sent from the measuring system 120 to the eye 114 and response beams (for example fluorescent light) running in the opposite direction. As described above, however, other types of measurement signals 144 are also possible, and can be used to infer the glucose concentration in an eye fluid of the eye 114.

Accordingly, FIG. 1 symbolically shows the "positioning signals" 146 as straight, dashed double arrows between the positioning system 122 and the eye 114. What has been said for the measurement signals 144 applies here accordingly. As examples of positioning signals, beam progressions are shown between the positioning system 122 and the pupil 148 of the eye 114, the positioning sensor 118 and the ocular sensor 116. Other regions of the eye 114 can also be sensed, as can known shapes of the eye, for example. Again, the embodiment of the positioning signals 146 as double arrows is to be understood merely symbolically, since unidirectional signal transmission (for example a purely visual signal) between the eye 114 and the positioning system 122 is also possible, for example. The various measurement principles which can be used in the positioning system 122 in order to determine a spatial positioning of the handheld measuring appliance 112 relative to the eye 114 have already been listed above and will therefore not be repeated at this juncture. Some examples are illustrated below.

Figure 2A:
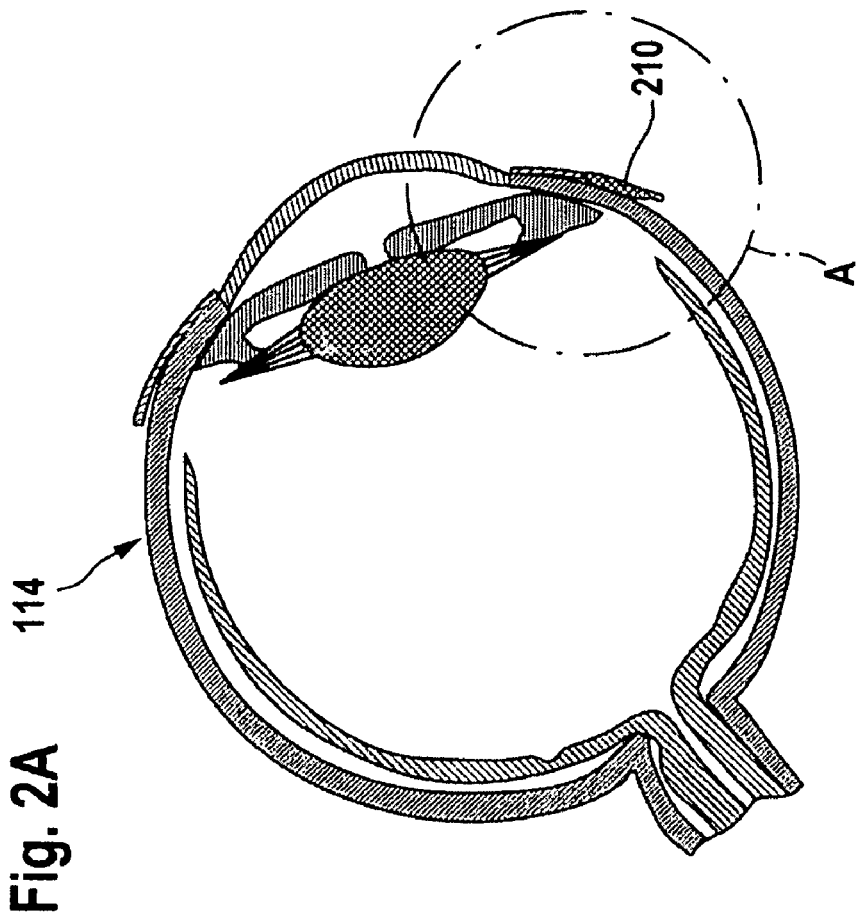
FIG. 2A shows an exemplary embodiment of an implanted ocular sensor for use in an analytical measuring system.
Figure 2B:
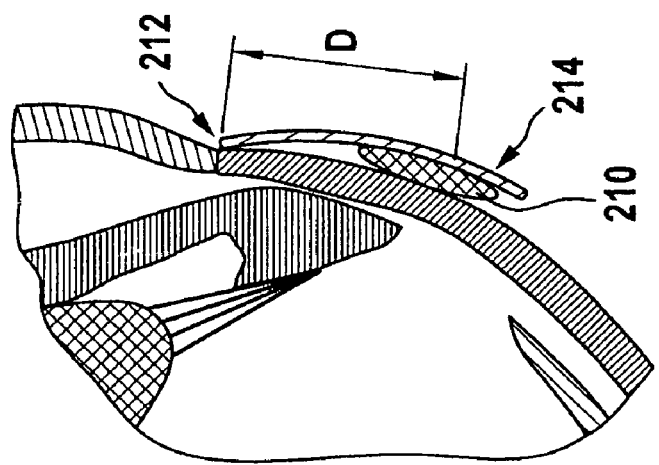
FIG. 2B shows an illustration of a detail in the form of excerpt A from the illustration shown in FIG. 2A.
Figure 3:
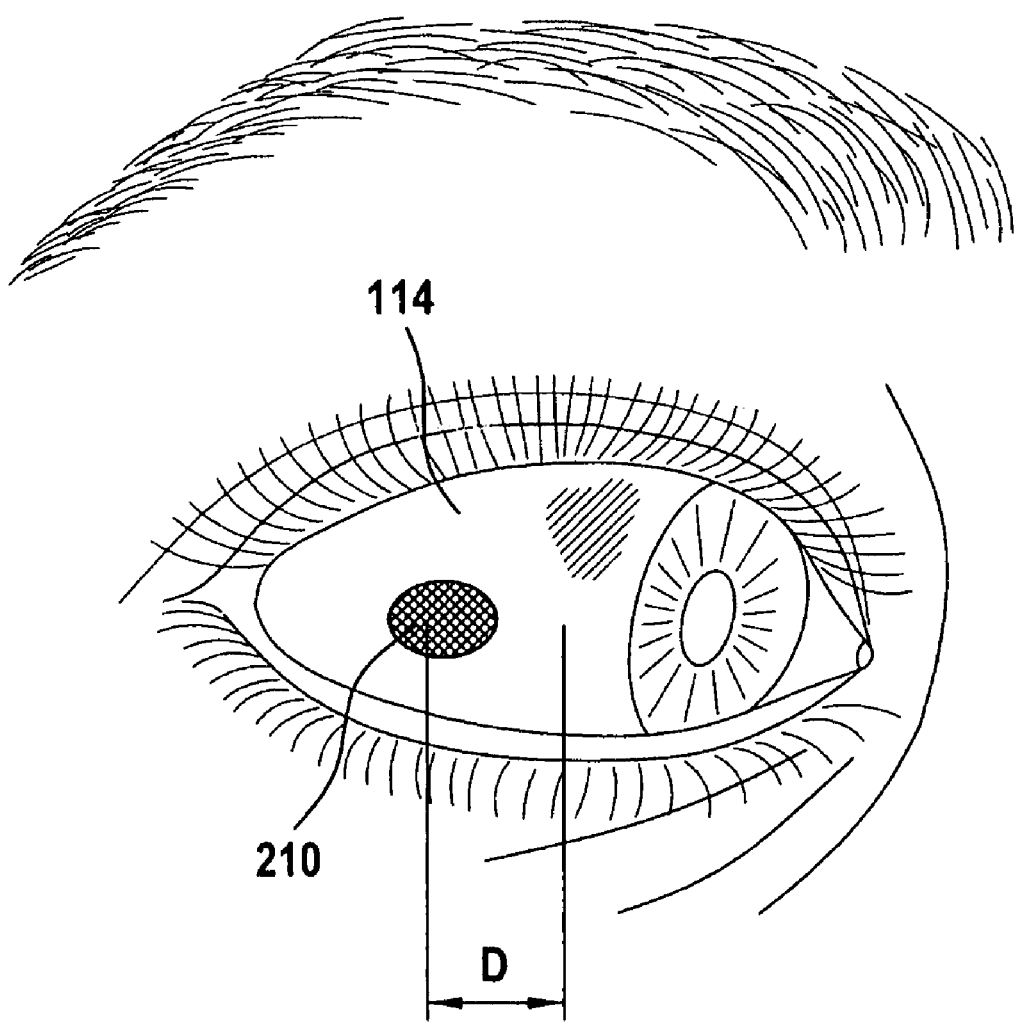
FIG. 3 shows a placement of an ocular sensor in a human eye.

As mentioned above, the analytical measuring system 110 in the example shown in FIG. 1 is based on an ocular sensor 116 and on a positioning sensor 118. FIGS. 2A, 2B and 3 show examples of such sensors 116, 118 which are in the form of implanted eye lenses. For this purpose, the dimensions and composition of the eye lenses are in a form such that the eye lenses can be implanted. Appropriate materials and dimensions are known from the prior art.

FIG. 2B shows a view of a detail of the illustration in FIG. 2A. The eye lens 210 is inserted underneath the conjunctiva 214 at a distance D, preferably 6 mm, from the limbus 212. By way of example, this simple operation affords the advantage over the use of contact lenses, which is alternatively or additionally possible, that the eye lens 210 (ocular sensor 116 and/or positioning sensor 118) is accommodated at a fixed location in the eye 114. The positioning and/or the measurement of the at least one analyte become accordingly more precise, since both measurements are typically highly dependent on the position of the eye lens 210. The illustration in FIG. 3 again shows that in this example the eye lens 210 is in a horizontal plane with the pupil 148 (other positionings are also possible) which means that the patient needs to look in the direction of the nose for the purpose of measuring the eye lens 210. Accordingly, the two illustrations in FIGS. 2A and 2B are sectional illustrations in this horizontal plane through the pupil 148 and the eye lens 210.

As exemplary embodiments of the design of the eye lens 210, reference is made by way of example to the ocular sensor described in WO 01/13783 A1. It goes without saying that other embodiments are also possible. Advantageously, the eye lens 210 additionally has a reference colorant homogenously admixed with it which does not change its fluorescence properties with the glucose concentration which is to be measured. Advantageously, this reference colorant can be excited at the same wavelength as the "donor" colorant, which is sensitive to the glucose concentration, in the eye lens 210. Excitation at different wavelengths is also possible. By way of example, the colorant tetramethylrhodamine (TMR) can be used, which is introduced into the eye lens 210. When measuring using the measuring system 120, which can receive both a signal from the donor and a reference signal, quotient formation between these signals allows a significant reduction in the dependency of the measurement of the analyte concentration on the distance between the handheld measuring appliance 112 and the eye 114 and/or the angle and/or the excited volume within the eye 114. Nevertheless, in practice there is a high level of dependency of the measurement signals and hence the measurement accuracy of the determination of concentration between this distance, the various angles and/or the excitation volume.

In order to reduce this additional dependency, the positioning system 122 shown symbolically in FIG. 1 is used. FIGS. 4A to 4C, 5A to 5B, 6 and 7 show various principles which can be used for determination of the spatial positioning by the positioning system 122.

Figure 4A:
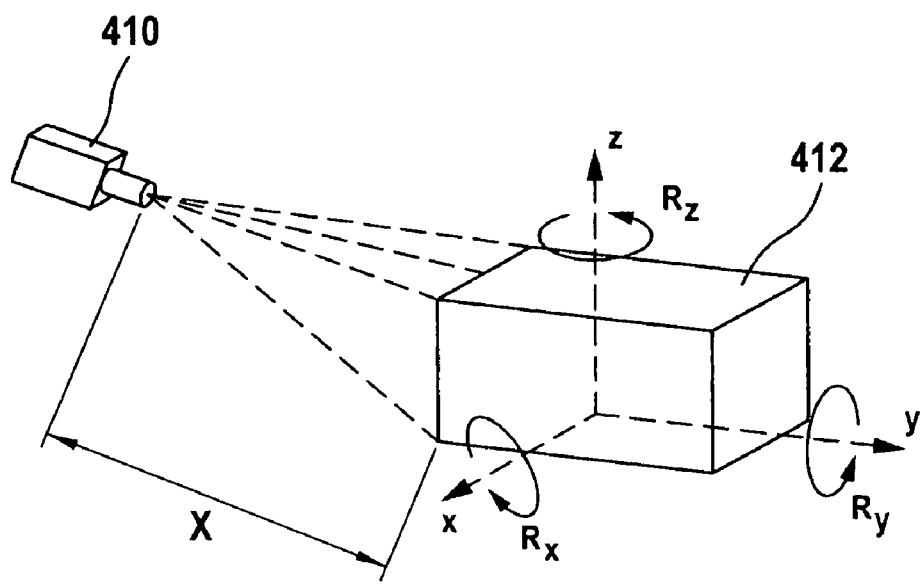
FIG. 4A shows a schematic illustration of a positioning measurement of a three-dimensional body using a camera.
Figure 4B:
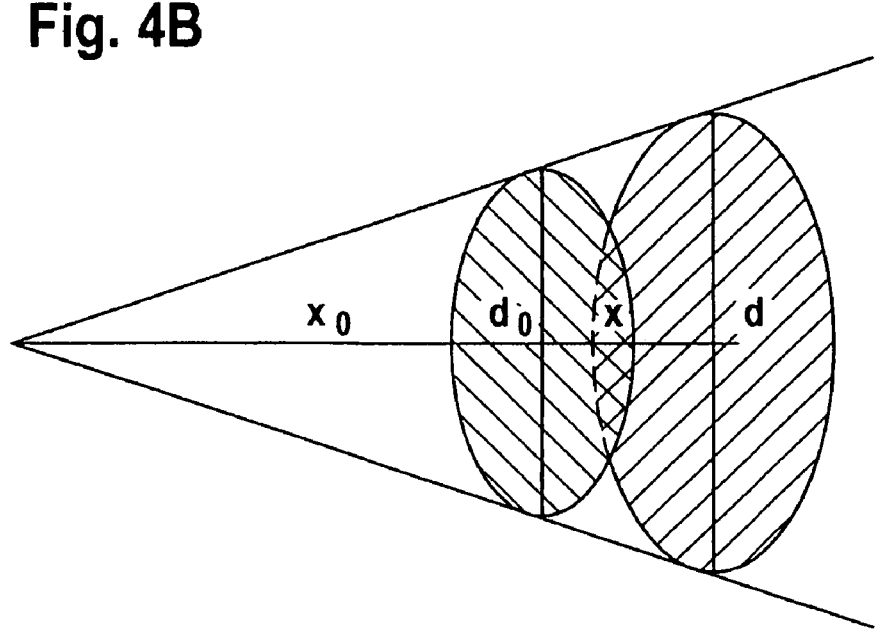
FIG. 4B shows a simple example of a distance measurement using geometric variables.
Figure 4C:
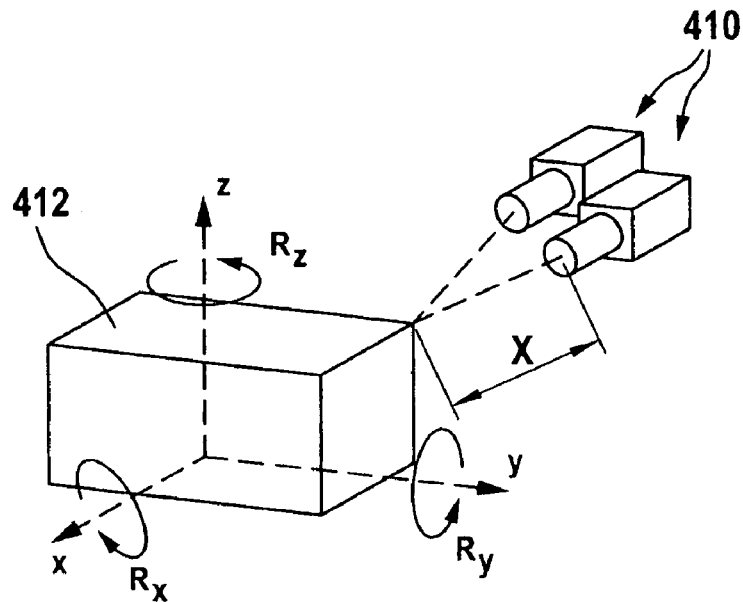
FIG. 4C shows a simple exemplary embodiment of a stereoscopic system.

FIGS. 4A to 4C show various camera systems for this purpose. These camera systems comprise at least one camera 410, wherein the positioning system 122 comprises a monocular camera 410 in the illustration shown in FIG. 4A and a binocular camera 410 in the illustration shown in FIG. 4C. The binocular camera system can be produced by two or more different cameras 410 or by appropriate mirror systems in conjunction with a single camera. Such systems are known to a person skilled in the art.

The systems shown in FIGS. 4A and 4B can be used to sense a distance X between the cameras 410 and a body 412 which is to be considered, and additionally further positioning coordinates. As shown symbolically in FIGS. 4A and 4C, these positioning coordinates may comprise various angles of rotation $R_X$, $R_Y$, $R_Z$, for example. In this case, the choice of coordinate system is arbitrary and a matter of expediency. Instead of a rotation of the body 412, it is accordingly also possible for a rotation of the camera 410 to be sensed, with the result that, by way of example, the origin of the coordinate system can also be put into the (or one of the) cameras 410. The measurement location on the body 412 is also comparatively arbitrary and can be stipulated accordingly.

The cameras 410 are preferably equipped with an image acquisition system (not shown in FIGS. 4A to 4C). This image acquisition system can identify appropriate edges of the body 412, for example, and can accordingly infer the positioning of the body 412 from these edges. For this purpose, the known shape of the body 412 is prescribed for the positioning system 122, for example.

FIG. 4B symbolically shows how, by way of example, a monocular system as shown in the illustration in FIG. 4A can be used to infer the distance X using a simple beam set when the size of the body 412 is known. If a circular sensor implant in the form of an eye lens 210 is considered, for example, the ratio of actual diameter d to nominal diameter $d_0$ when mapped on a camera chip is a function of the current distance X. In the simplest case:

$$X = d \cdot X_0 / d_0$$

If the camera chip or the camera 410 is tilted with respect to the eye lens 210, assumed to be a disk for simplicity, the circular disc becomes an ellipse in the map. From the ratio of minor axis d' to major axis d, the tilt angle α, for example, can be determined as:

$$\alpha = \frac{d'}{d}$$

In the case of the binocular system with the two cameras 410 shown in FIG. 4C, the measurement location is considered by the two cameras 410 from different viewing angles. From the displacement of the generated images with respect to one another, an appropriate triangulation algorithm can be used to determine the position and/or tilt of the body 412. Such triangulation systems have the advantage over the monocular systems shown in FIG. 4A that the shape or the map of the destination does not necessarily need to be stored in the image acquisition system.

Figure 5A:
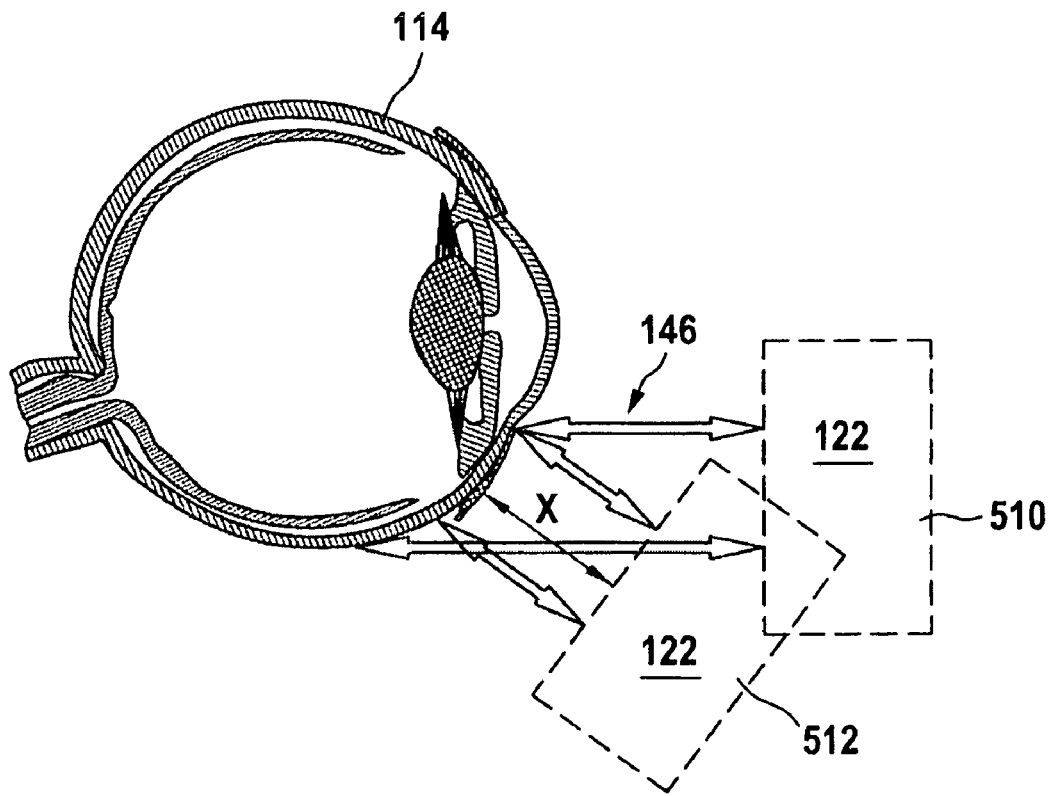
FIG. 5A shows a basic illustration of a propagation-time-based positioning measurement.
Figure 5B:
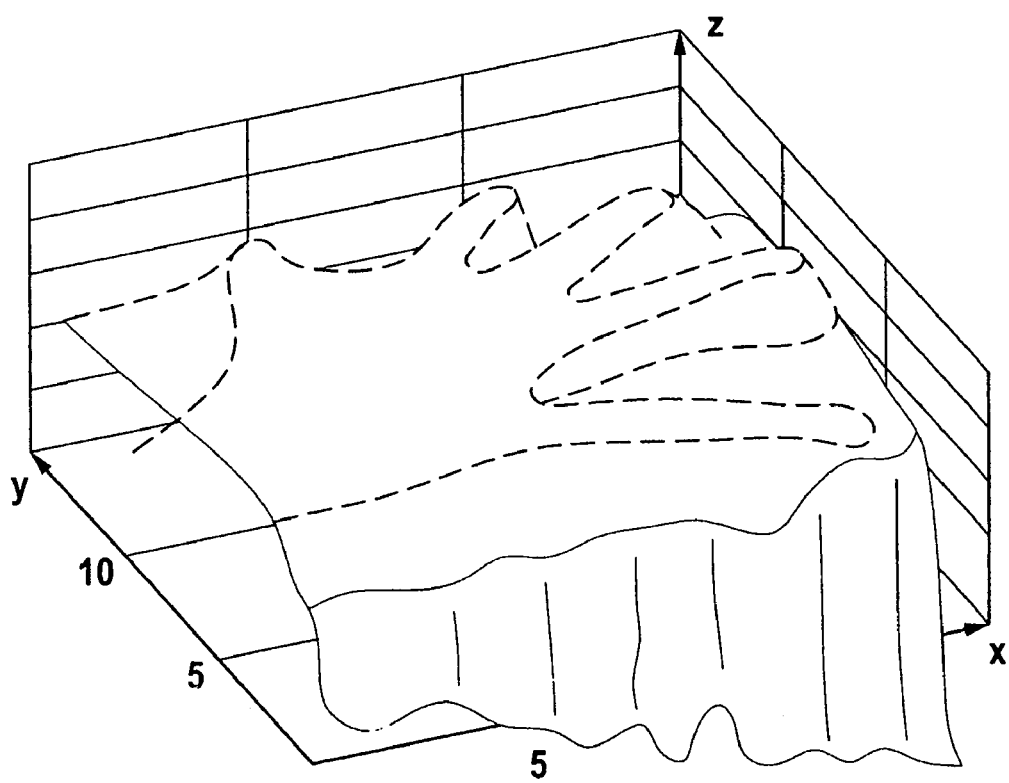
FIG. 5B shows an example of a propagation time measurement using photomix detectors (PMDs)

FIGS. 5A and 5B show a further measuring principle which can be used by the positioning system 122. This case involves a propagation-time-based system in which positioning signals 146 (for example laser pulses, acoustic signals, infrared signals or radar signals) can be sent from the positioning system 122 to the destination on the eye 114. The propagation time of the signals respectively reflected by the eye 114 is measured in this case. By way of example, the measurement can be made from two, three or more positions. Accordingly, from the first position, denoted by 510 in FIG. 5A, it is possible to establish a difference in the propagation time between the positioning signals 146 emitted and reflected at that point, whereas in the second position, denoted symbolically by 512, the two positioning signals 146 (in practice there are typically more than two) do not have different propagation times. From the measured propagation time and the propagation time differences, it is not only possible to determine the distance X between the positioning system 122 and the eye 114, but rather it is also possible to ascertain the spatial orientation of the positioning system 122 relative to the eye 114, for example.

It is also possible to take a measurement using a single positioning signal 146 or a single positioning beam and to take a measurement from fewer than three different positions. In this case, to obtain further information, the measurement location on the eye 114 can be run over (scanned), for example, using the positioning signal 146. In this way, it is again finally possible to attain more than three positions. This measuring principle is used commercially by what are known as photomix detectors (PMDs). In PMDs, the signal propagation time (instead of the grayscale value in a camera) is determined per pixel in a pixel array, in a similar manner to a CCD or CMOS camera, and hence a three-dimensional profile is produced. An example of such a measurement is shown in FIG. 5B. Whereas the X and Y axes show an arbitrary spatial position, the Z axis indicates the propagation time, which has been measured using a PMD. Similarly, it is also possible to capture contours of an eye, for example, with the result that not only the distance between the positioning system 122 but also, additionally, angular positions of the eye 114 and/or of the positioning system 122 relative to one another can be ascertained, for example.

A further measuring principle which can be utilized by the positioning system 122 is the measurement of signal intensities. If a divergent, electromagnetic (or alternatively or additionally also acoustic, for example) beam is radiated onto an object, a portion of this beam is reflected divergently. The intensity of the divergent reflected beam is a function of the distance and can therefore be used to measure range. Also by way of example, a fluorescent light source at the irradiation location usually produces divergent fluorescent light, the intensity of which can be measured by the positioning system 122 and used for determining distance. This measuring principle for determining distance can be used, by way of example, to sense the intensity of the fluorescent light from a reference fluorophor in the eye lens 210 and from this to determine the distance between the positioning system 122 and the location of the eye lens 210.

Figure 6:
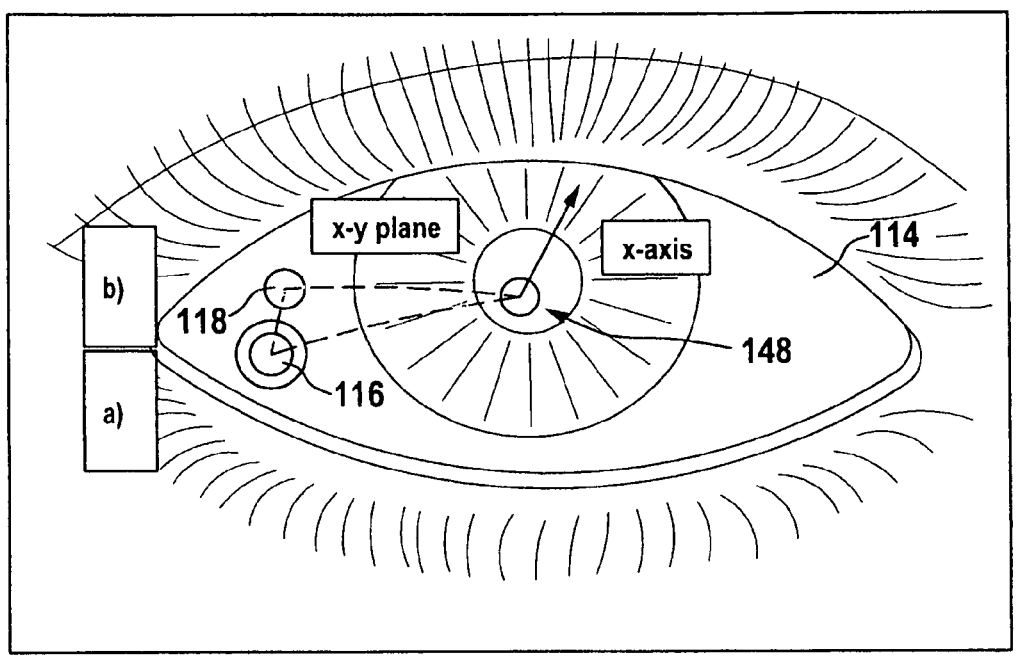
FIG. 6 shows an example of an implanted ocular sensor and of an additional implanted positioning sensor.

If the intensity of the reflected beam and/or the fluorescence is measured at more than one location, it is possible—as used by the invention—to obtain additional positioning information. An example of such a measurement is shown in FIG. 6. In this case, firstly the fluorescence of the ocular sensor 116 and also the fluorescence of the positioning sensor 118 and the intrinsic fluorescence of the cornea in the region of the pupil 148 are sensed. By sensing the fluorescence intensities from these three locations, in similar fashion to the propagation time measurement described above, this allows three-dimensional distance and/or other positioning information (for examples angles) to be obtained. Implementations of intensity measurements other than the embodiment shown in FIG. 6 can also be used. The fluorescence intensity can also be picked up using a CCD camera, for example, in order to simultaneously obtain information about the intensities at different locations. Alternatively or in addition, it is also possible to use different sensors for the pickup, for example sensors with different color sensitivities.

Figure 7:
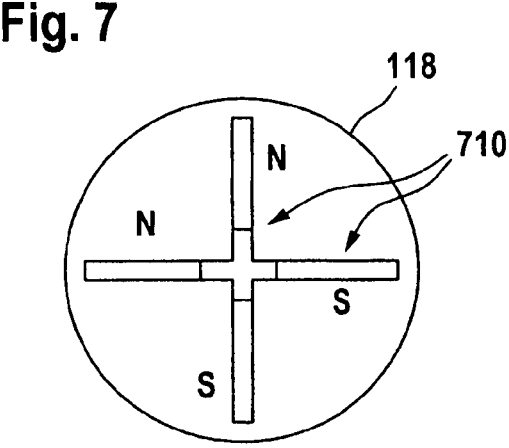
FIG. 7 shows an example of a positioning sensor with magnetization for measuring spatial positioning.

FIG. 7 shows a further example of a measuring principle which can be used for the positioning system 122. In this case, magnetic field measurements are used which are based on magnetoresistive sensors (for example GMR sensors), for example. Such sensors can be used to determine the relative position of a sensor incorporated in the positioning system 122 with respect to a magnetic field. Such a magnetic field is produced using the positioning sensor 118 shown in FIG. 7, for example, which can be introduced into the eye 114 as a separate positioning sensor 118 in the form of an eye lens 210, or which—alternatively or in addition—may also be part of the ocular sensor 116. In the example shown in FIG. 7, ferromagnetic or magnetizable microparticles or nanoparticles are printed onto the positioning sensor 118 using a printing method (for example using pad printing or the like). Specific north/south magnetization 710 is used to obtain a measurement reference for two magnetoresistive sensors arranged in crossed fashion in the positioning system 122 which are able to be used to determine the angular position between the magnetoresistive sensors and the positioning sensor 118. From the signal strength, which is averaged overall, for example, it is additionally also possible to infer the distance between the positioning sensor 118 and the magnetoresistive sensors in the positioning system 122. This allows information about the spatial positioning to be obtained.

The above-described exemplary embodiments of measuring principles on which the positioning system 122 can be based are merely a few possibilities which can be used. The method described and also further methods can also be combined with one another in many cases. Particularly the combination of intensity measurements and camera systems and also propagation time measurements and camera systems, for example in the form of PMDs, are suitable for position finding.

FIGS. 8 to 16 show various exemplary embodiments of the analytical measuring system 110 with a handheld measuring appliance 112.

Figure 8:
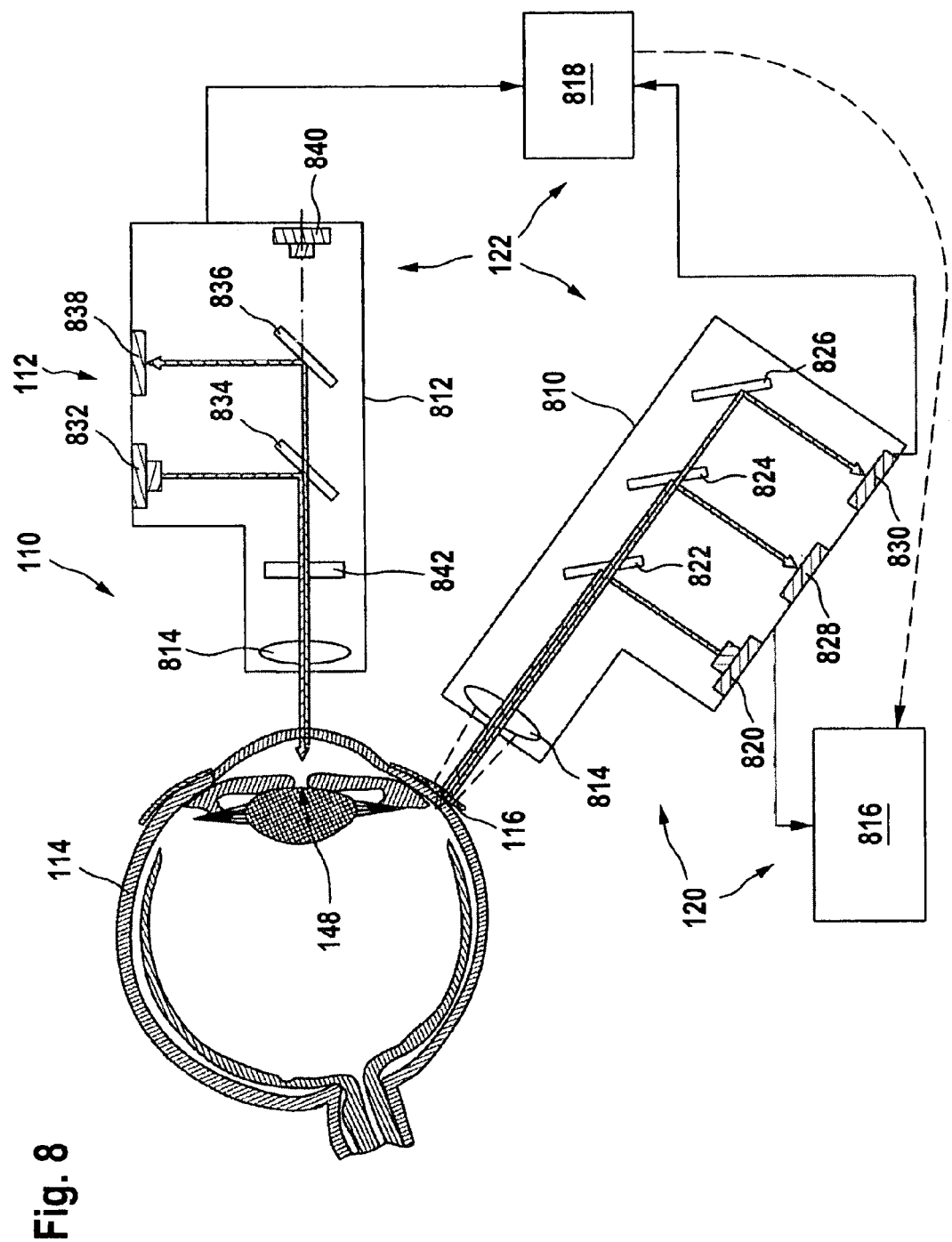
FIGS. 8 to 16 show exemplary embodiments of analytical measuring systems with handheld measuring appliances in different forms.

In the exemplary embodiment shown in FIG. 8, two separate optical units are used: A measuring unit 810 and a pilot unit 812. Both units 810, 812 are equipped with an optical system, particularly a confocal optical system, which in this case is indicated merely symbolically by the lenses 814. Another embodiment of the optical system is also conceivable. Whereas the measuring unit 810 is oriented to the implanted ocular sensor 116, the pilot unit 812 is oriented to the pupil 148. The information generated by the measuring unit 810 is processed by a measurement evaluation section 816, whereas a positioning evaluation section processes information both from the measuring unit 810 and from the pilot unit 812. The measurement evaluation section 816 and the relevant optical components of the measuring unit 810 are therefore part of the measuring system 120, whereas the positioning system 122 comprises the pilot unit 812, the positioning evaluation section 818 and also parts of the measuring unit 810.

The measuring unit 810 in the exemplary embodiment shown in FIG. 8 is designed to use confocal fluorescence excitation at a single wavelength to measure the analyte concentration (for example glucose) for a donor, which the ocular sensor 116 contains, and also a reference. For this purpose, the measuring unit 810 comprises an excitation light emitting diode 820 which generates light at a wavelength which can be used to excite both the donor and the reference colorant in the ocular sensor 116. This excitation light from the excitation light emitting diode 820 is deflected by a dichroic mirror 822 tuned to the excitation wavelength of the excitation light emitting diode 820 and is focused onto the ocular sensor 116 by means of the lens 814 (or a corresponding optical system) such that the focusing has a smaller diameter than the ocular sensor 116 itself. The fluorescent light generated in this manner from the reference colorant or from the donor which is sensitive to the analyte to be demonstrated is accordingly emitted by the ocular sensor 116, concentrated by the lens 814 and in turn enters the measuring unit 810. The dichroic mirror 822 is set up such that this fluorescent light, which usually has longer wavelengths than the excitation light from the excitation light emitting diode 820, passes through this dichroic mirror 822 without being reflected. Accordingly, the measuring unit 810 contains two further dichroic mirrors 824 and 826 whose reflection properties are set such that they isolate the fluorescent light from the donor from that of the reference. Accordingly, the donor fluorescent light is reflected onto a donor photodiode 828, whereas the reference fluorescent light is reflected by the dichroic mirror 826 onto the reference photodiode 830.

By means of a comparison of the signals from the reference photodiode and from the donor photodiode, possibly on the basis of the excitation intensity of the excitation light emitting diode 820, it is then possible to use the measurement evaluation section 816 to infer the analyte concentration in the eye fluid in the region of the ocular sensor 116. For details of this measurement, it is possible to refer to WO 01/13783 A1, for example.

As described above, usually the result of this concentration measurement is dependent on the distance of the handheld measuring appliance 112 from the ocular sensor 116 or on an orientation of the handheld measuring appliance 112 relative to the eye 114, particularly an orientation of the measuring unit 810, however. To compensate for these inaccuracies and to measure the spatial positioning, the positioning system 122 is used. In this case, in the setup shown in FIG. 8, a measuring method is used to determine the positioning which is based on the measurement of two fluorescence intensities. The first, positioning-dependent intensity signal used is the signal from the reference photodiode 830, which is independent of the analyte concentration and merely depends on the distance or the orientation between the measuring unit 810 and the eye 114. A second positioning-dependent signal is generated using the pilot unit 812. This pilot unit 812 has a pilot light emitting diode 832 which generates excitation light at a wavelength which excites the pupil 148 of the eye 114 to fluoresce. Hence, the pupil 148 is used as a second measurement point besides the ocular sensor 116 for positioning measurement.

The light from the pilot light emitting diode 832 is deflected by a dichroic mirror 834 tuned to the wavelength of the pilot light emitting diode 832 and is concentrated by the lens 814 in the direction of the pupil 148. Since it usually has a longer wavelength, fluorescent light emitted by the pupil 148 is allowed to pass by the appropriately set dichroic mirror 834 and impinges on the further dichroic mirror 836, which is tuned to the wavelength of the fluorescent light from the pupil. From there, this fluorescent light is routed onto the pilot photodiode 838, where it is converted into an electrical signal.

Since the signal from the pilot photodiode 838 is dependent on the distance or the orientation of the pilot unit 812 relative to the pupil 148, this signal provides a further piece of important positioning information besides the signal from the reference photodiode 830. From the comparison of these two intensity signals from the reference photodiode 830 and the pilot photodiode 838, it is possible for a piece of positioning information to be obtained in the positioning evaluation section 818. Since each of the two signals from the photodiodes 830 and 838, taken alone, can be converted into a piece of distance and/or angle information, the information from the two photodiodes 830, 838, together, provides at least one additional positioning coordinate, for example an angular orientation.

However, it should be pointed out that in practice there is no absolute necessity for exact conversion into positioning coordinates. Rather, the handheld measuring appliance 112 can also operate such that a positioning in which both signals, that is to say the signal from the reference photodiode 830 and the signal from the pilot photodiode 838, exceed a prescribed threshold for a prescribed excitation intensity of the diodes 820 and 832, the positioning is identified as being correct. It is also possible for "target corridors" for the measured intensities to be prescribed. Accordingly, by way of example, the positioning evaluation section 818 can directly or indirectly trigger a measurement by the measuring unit 810 and the measurement evaluation section 816.

The measurement evaluation section 816 and the positioning evaluation section 818 may be separate electronic units. However, they may also be components of the central computation unit 136 shown in FIG. 1 and may accordingly be wholly or partly in the form of software components (for example program modules) for example.

In addition, the pilot unit 812 in the exemplary embodiment in FIG. 8 also contains a flat illumination element (backlight) 840 and a transparent display element 842. Depending on the embodiment of the pilot unit 812, these may serve different purposes and may be in different forms. In the simplest case, the transparent display element 842, for example, may contain a reticle, for example simple cross-hairs in the optical path. Using these cross-hairs, the patient looking into the pilot unit 812 can effect course positioning. In this case, the patient sees, for example on the basis of reflective properties of the transparent display element 842, the pilot photodiode 838 and/or the backlight 840, an image with the cross-hairs overlaid onto it. By way of example, the patient can simultaneously look at light spots from the pilot light emitting diode 832 and the backlight 840, with the cross-hairs superimposed on them. Accordingly, he can manually effect course positioning of the handheld measuring appliance 112 such that, by way of example, the light spots are oriented concentrically and the cross-hairs are oriented centrically in this concentric arrangement.

Another option is for the transparent display element 142 to be used to overlay additional information. For this purpose, this display element may contain a liquid crystal display element and/or other display elements, for example, which can be used to transmit a piece of positioning information to the patient, for example. This may be arrows, for example, which are overlaid in order to signal that the handheld measuring appliance 112 needs to be moved and/or tilted in an appropriate direction in order to achieve correct positioning. The information reproduced can be generated by the positioning system 122, for example.

In the embodiments described, the transparent display element 842 and the backlight 840 thus form components of the feedback unit 124 (see FIG. 1). Further elements of the handheld measuring appliance 112, such as the operator control unit 130 and/or the calibration system 128, are not shown in FIG. 8. For the way in which these possible further elements work, reference is made to the description relating to FIG. 1.

As an alternative to the measuring principle shown in FIG. 8 for the measuring unit 810, it should also be pointed out that the donor and the reference fluorophor in the ocular sensor 116 do not necessarily need to be excited using the same excitation light emitting diode 820. Thus, instead of the arrangement of the measuring unit 810 shown in FIG. 8, there may also be a system provided in which not only the excitation light emitting diode 820 for the donor but also an additional excitation light emitting diode is provided (not shown in FIG. 8) which is specifically tuned to the excitation wavelength of the reference fluorophor in the ocular sensor 116. Accordingly, a further dichroic mirror could be provided, for example, which is tuned to the reflection of the excitation light emitted by this reference light emitting diode. The design corresponds to the design in FIG. 8, wherein only a further "arm" of the design which is in the form of a three-armed fan in FIG. 8 would be added to the measuring unit 810, which means that a "4-armed" design would be produced. This is not shown in the drawing.

Figure 9:
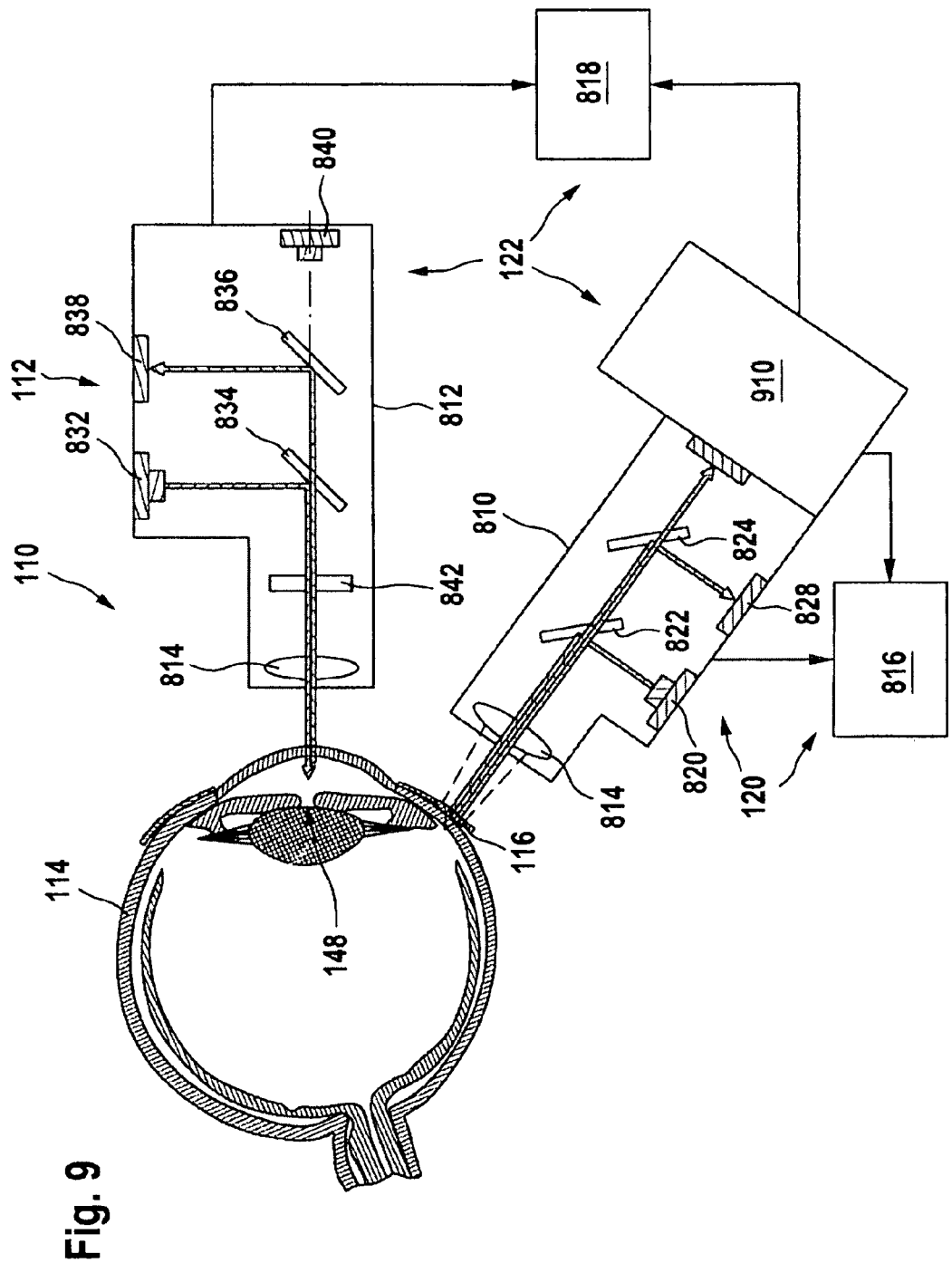

FIG. 9 shows a second exemplary embodiment of an analytical measuring system 110 with a handheld measuring appliance 112 and an ocular sensor 116. The design corresponds essentially to the design shown in FIG. 8, which means that again a measuring unit 810 and a pilot unit 812 are provided. One difference over the measuring unit 810 in the exemplary embodiment shown in FIG. 9, however, is that in this case the reference photodiode 830 has been replaced by a camera 910 in the form of a CMOS camera. Accordingly, the dichroic mirror 826 can also be dispensed with, for example, which means that fluorescent light from the reference fluorophor is projected from the ocular sensor 116 directly into the image area of the camera 910. Alternatively, an appropriate dichroic mirror for this reference fluorescent light may also be provided, however.

In contrast to picking up the reference fluorescent light using a reference photodiode 830 as in the design in FIG. 8, the camera 910 is now used to pick up not only a piece of intensity information but also a two-dimensional pattern (array) of intensity information on the CMOS chip of the camera 910. This means that it is possible, for example using an image evaluation system (which the positioning evaluation section 818 contains, for example), to also obtain additional spatial information, for example in line with the above description relating to FIGS. 4A to 4C. Alternatively or in addition, it is also possible to average the intensity over entire image areas.

The information from this camera 910 is made available to the positioning evaluation section 818, which means that the camera 910, the positioning evaluation section 818 and the pilot unit 812 (which is of similar design to that in FIG. 8, for the manner of operation see above) are components of the positioning system 122. This allows additional information about the positioning to be generated. By way of example, the camera 910 can be used to observe the focused spot of the excitation light generated by the excitation light emitting diode 820 on the ocular sensor 116, to determine the correct positioning (for example a concentric positioning within a circular eye lens 210) and to trigger a measurement by the measuring system 120 accordingly. In addition, the intensity measurement by the pilot unit 812 can be taken into account. By way of example, the intensities can also be ascertained in succession, which means that, by way of example, the pilot unit 812 is first of all used to produce a pilot signal for the coarse positioning so as subsequently to be able to perform fine positioning using the camera 910. Such systems have a high level of precision and accordingly result in very highly reproducible measurements of the analyte concentration.

In similar fashion to the description based on FIG. 8, the system shown in FIG. 9 can be modified by using different excitation light emitting diodes to excite the donor and the fluorescence reference. Accordingly, the design of the measuring unit 810 could have a further excitation light emitting diode added to it which is tuned to the excitation wavelength of the reference fluorophor in the ocular sensor 116. A further dichroic mirror would also be advantageously added in this case. This means that the reference fluorophor and the donor do not necessarily need to be chosen such that they have a common excitation wavelength, this additionally increasing flexibility in terms of the selection of these materials.

Figure 10:
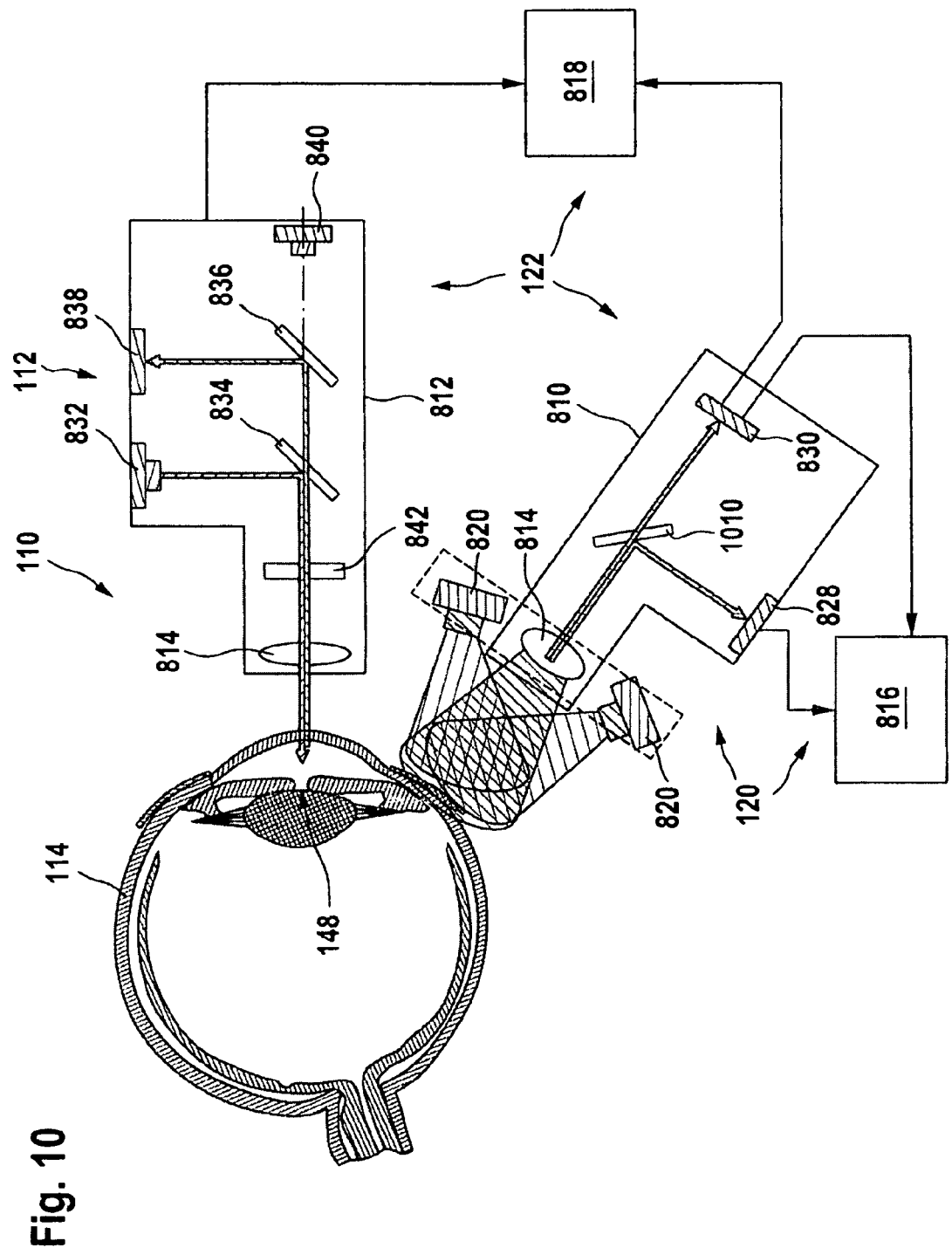

FIG. 10 shows an alternative modification to the analytical measuring system 110 in comparison with FIGS. 8 and 9. The pilot unit 812 is again based on the embodiments in FIGS. 8 and 9, which means that reference can be made to the description above. In contrast to the previous exemplary embodiments, however, the exemplary embodiment shown in FIG. 10 has the measuring unit 810 modified such that instead of an individual excitation light emitting diode 820 a ring of excitation light emitting diodes 820 arranged around the lens 814 of the measuring unit 810 is now used. The excitation light from said excitation light emitting diodes is now no longer, as in FIGS. 8 and 9, concentrated by the lens 814 and focused onto the ocular sensor 116. Accordingly, the measurement spot or the excitation area in the eye 114 is normally larger than the implant eye lens 210, which means that the eye lens 210 may be of very small diameter. Accordingly, the positioning of the implant during the implantation operation is not as critical as in the exemplary embodiments shown in FIGS. 8 and 9, for example. It has also been found that the measurement of the analyte concentration in such a design reacts less critically to the exact positioning of the handheld measuring appliance 112.

In line with the ring-shaped design of the excitation light emitting diodes 820 outside the lens 814, the internal optical design of the measuring unit 810 is also simplified. Instead of at least two dichroic mirrors, there is now only one dichroic mirror 1010 provided which isolates the fluorescent light coming from the donor from the fluorescent light coming from the reference fluorophor. These fluorescence components and the measurement thereof are picked up, in FIGS. 8 and 9, using the photodiodes 828 and 830. The further evaluation of the measurement or the measuring principle is based on the design in FIG. 8.

In FIG. 10 too, it is again possible—instead of excitation using a single wavelength range—for the donor and the reference fluorophor to be excited separately. Accordingly, not only the excitation light emitting diode 820 but also further excitation light emitting diodes may be provided, for example, which are tuned specifically to the excitation wavelength of the reference fluorophor. By way of example, in the annular arrangement of the light emitting diodes 820 around the lens 814, every second light emitting diode may be tuned to the excitation wavelength of the reference fluorophor.

Figure 11:
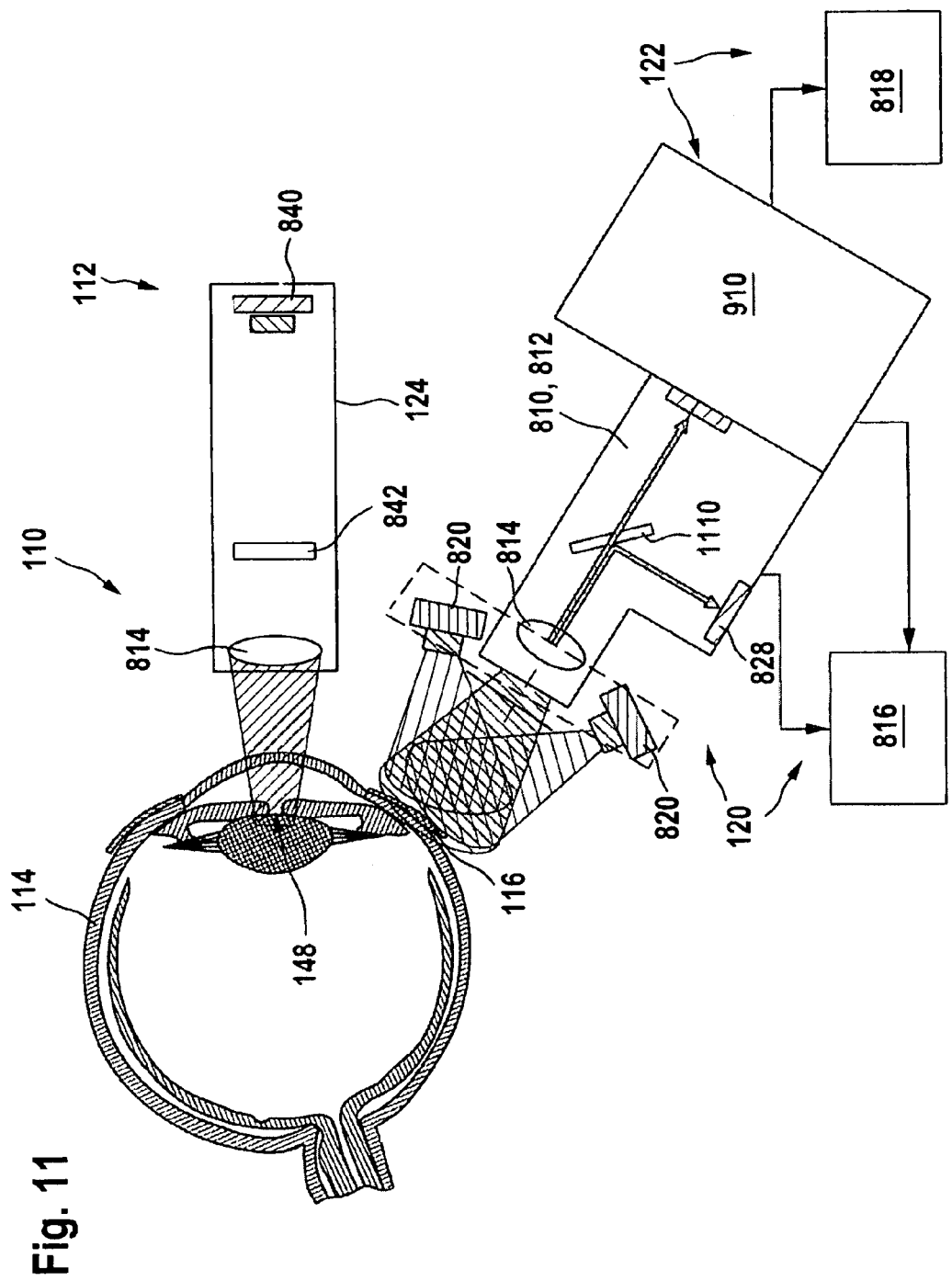

FIG. 11 shows an exemplary embodiment of an analytical measuring system 110 which combines the fundamental concepts of the exemplary embodiments in FIGS. 9 and 10. In this exemplary embodiment, the functions of the measuring unit 810 and the pilot unit 812 are performed by the same unit. In similar fashion to the embodiment in FIG. 10, the measuring unit 810 is again equipped with a ring of excitation light emitting diodes 820 which irradiate the region of the ocular sensor 116 in the form of an eye lens 210 over a large area. Fluorescent light emitted by the donor is reflected by the dichroic mirror 1110 and registered by the donor photodiode 828, in similar fashion to the embodiment in FIG. 10.

In contrast to FIG. 10, however, the reference photodiode (830 in FIG. 10) has been replaced by a camera 910—in similar fashion to the embodiment in FIG. 9. As described above, not only is it possible for this camera to be used to ascertain the intensity of the reference fluorescence (which is then, in common with the signal from the donor photodiode 828, used by the measurement evaluation section 816 to determine the analyte concentration), but it is also possible for the signal from the camera 910 to undergo image evaluation—in similar fashion to the description above of the manner in which the design in FIG. 9 works. This image evaluation generates an adequate piece of positioning information to allow accurate measurement. This is conditional, in particular, on the large-area illumination by the excitation light emitting diodes 820—as described above—producing lower positional sensitivity for the determination of the analyte concentration than in examples in which exact focusing takes place.

In addition, in the exemplary embodiment shown in FIG. 11, the handheld measuring appliance 112 also has the feedback unit 124 integrated in it. This feedback unit 124 in turn has the transparent display element 842 and the backlight 840, the transparent display element 842 being able to be supplied with information from the positioning system 822, for example, as described above with reference to FIG. 8. In this way, cross-hairs or a reticle, for example, in the transparent display element 842 can be used by the patient for coarse positioning of the handheld measuring appliance 112 before the positioning system 122 is then used to measure the spatial positioning further, to produce appropriate correction signals and/or to trigger a measurement by the measuring system 120.

Figure 12:
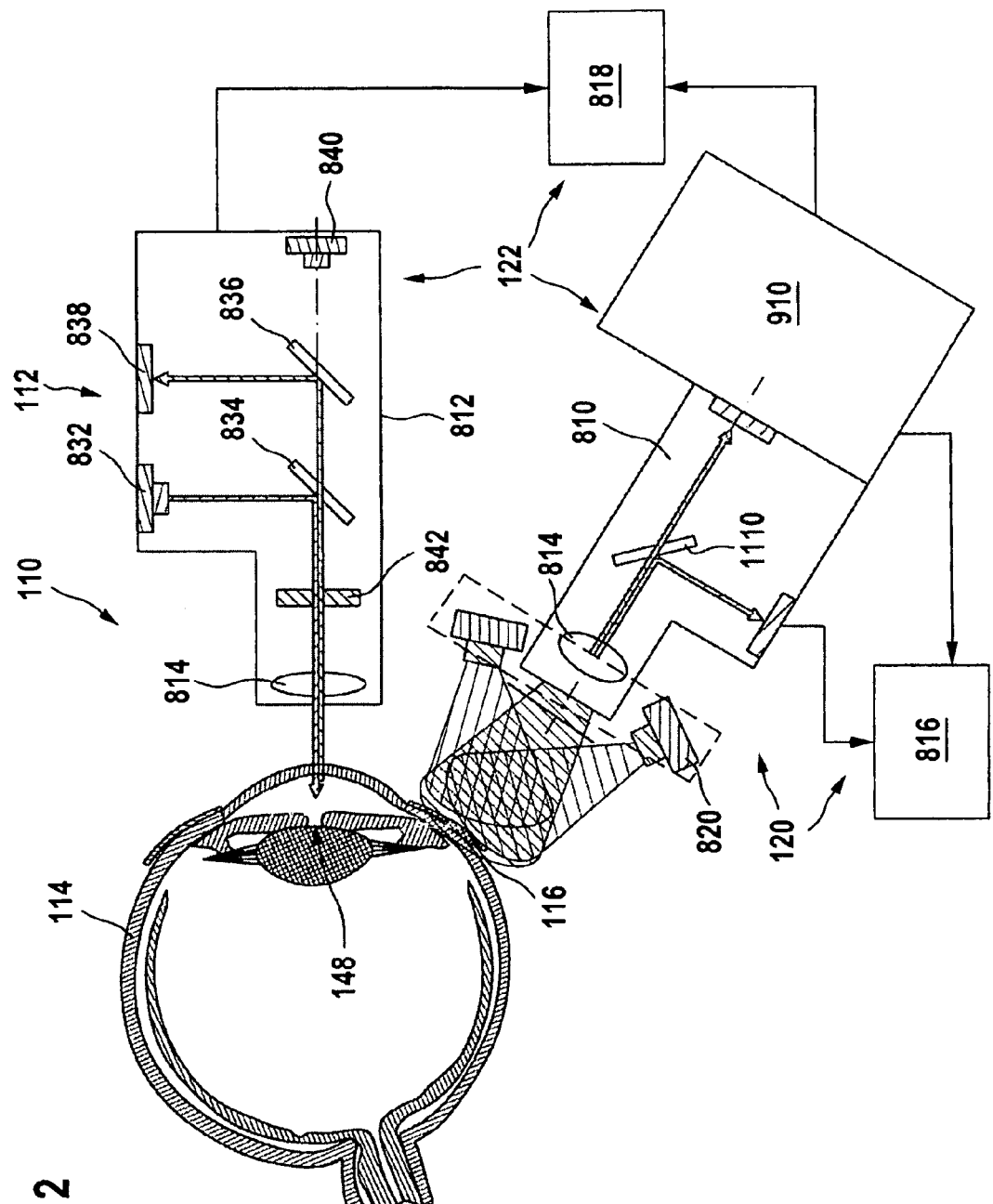

FIG. 12 shows an exemplary embodiment of the analytical measuring system 110, which combines a measuring unit 810 based on the exemplary embodiment in FIG. 11 with a pilot unit 812 based on the exemplary embodiment in FIG. 8. For the design and manner of operation of these units, reference is made to these figures. Accordingly, it is first of all possible to perform coarse positioning using the pilot unit 812, for example, whereupon fine positioning using the camera 910 is then performed. A simultaneous processing of the information from the pilot unit 812 and from the camera 910 to obtain positioning information by the positioning evaluation section 818 is also possible. Thus, by way of example, the pilot unit 812 can be used to perform distance measurement, whereas the camera 910 is then used to measure positioning with additional positioning coordinates. Again, the transparent display element 842 can be used for user information (feedback).

Figure 13:
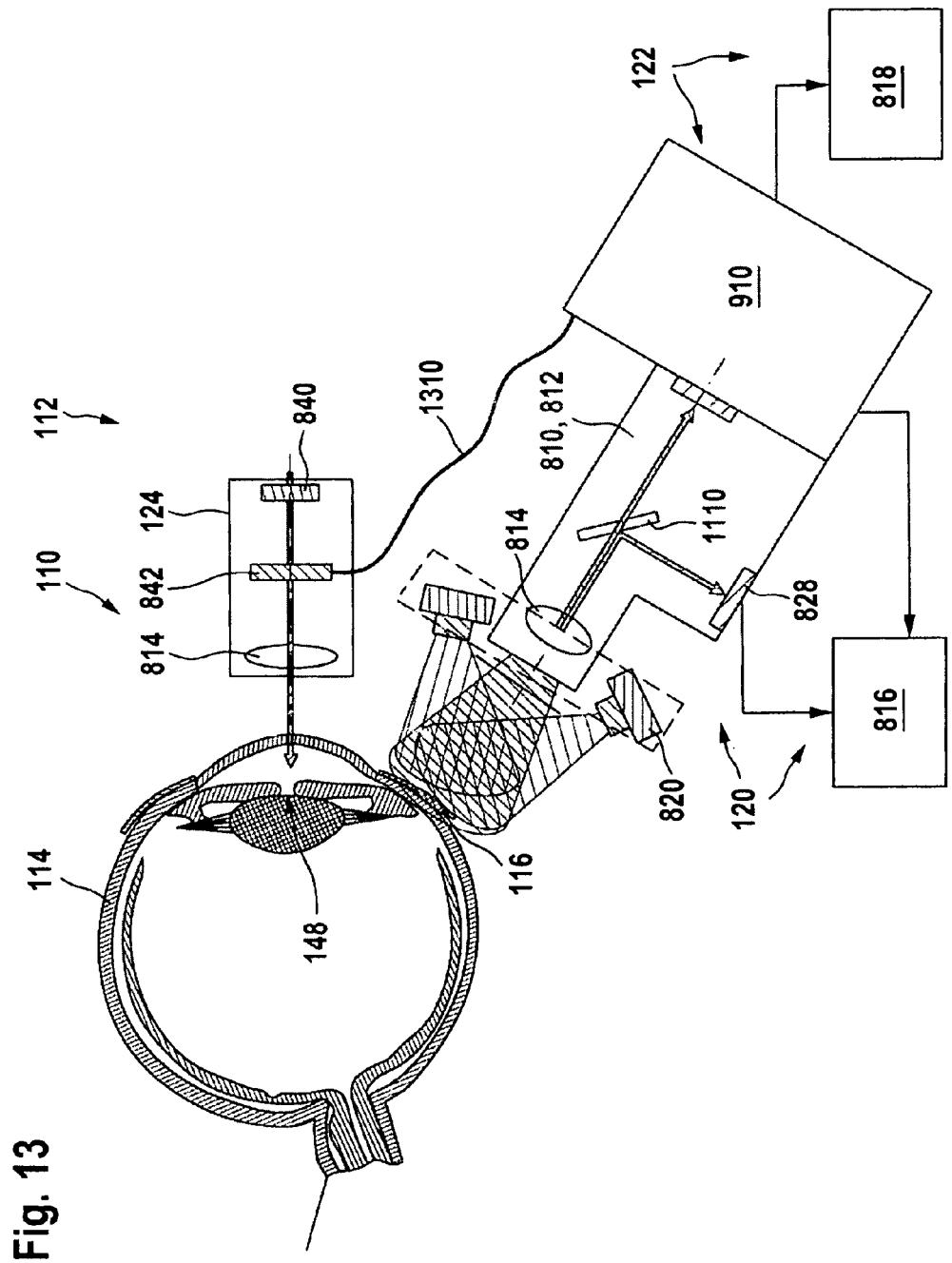

FIG. 13 shows an exemplary embodiment of an analytical measuring system 110 whose function and design largely correspond to the exemplary embodiment shown in FIG. 11. Again, in this case the measuring unit 810 and the pilot unit 812 are integrated in the same unit. Also, there is again a feedback unit 124 provided which provides the patient with information about the positioning and which has not only a lens 814 and a backlight 840 but also a transparent display element 842. As in FIG. 11 too, the design shown in FIG. 13 can also have cross-hairs, for example, overlaid over the transparent display element 842 for the purpose of coarse positioning. In addition, however, an image cable 1310 is used to load the camera image from the camera 910 directly onto the transparent display element 842, so that the user is provided with the image information as also "seen" by the positioning system 122 directly. By way of example, the eye 114 can then be fixed using the backlight 840 and the transparent display element 842, whereas the optimum distance between the handheld measuring appliance 112 and the eye 114 can be set using the image definition (for example the definition of the map from the ocular sensor 116) for example. Again, the positioning system 122 can then automatically trigger a measurement by the measuring system 120 as soon as an optimum distance is achieved and at least one further positioning coordinate is in a prescribed range. The information can be fed back to the patient directly via the camera image using the transparent display element 842. In addition, it is also possible to overlay additional information, such as measurement results, plausibility of the measurement, date, time, temperature etc.

Figure 14:
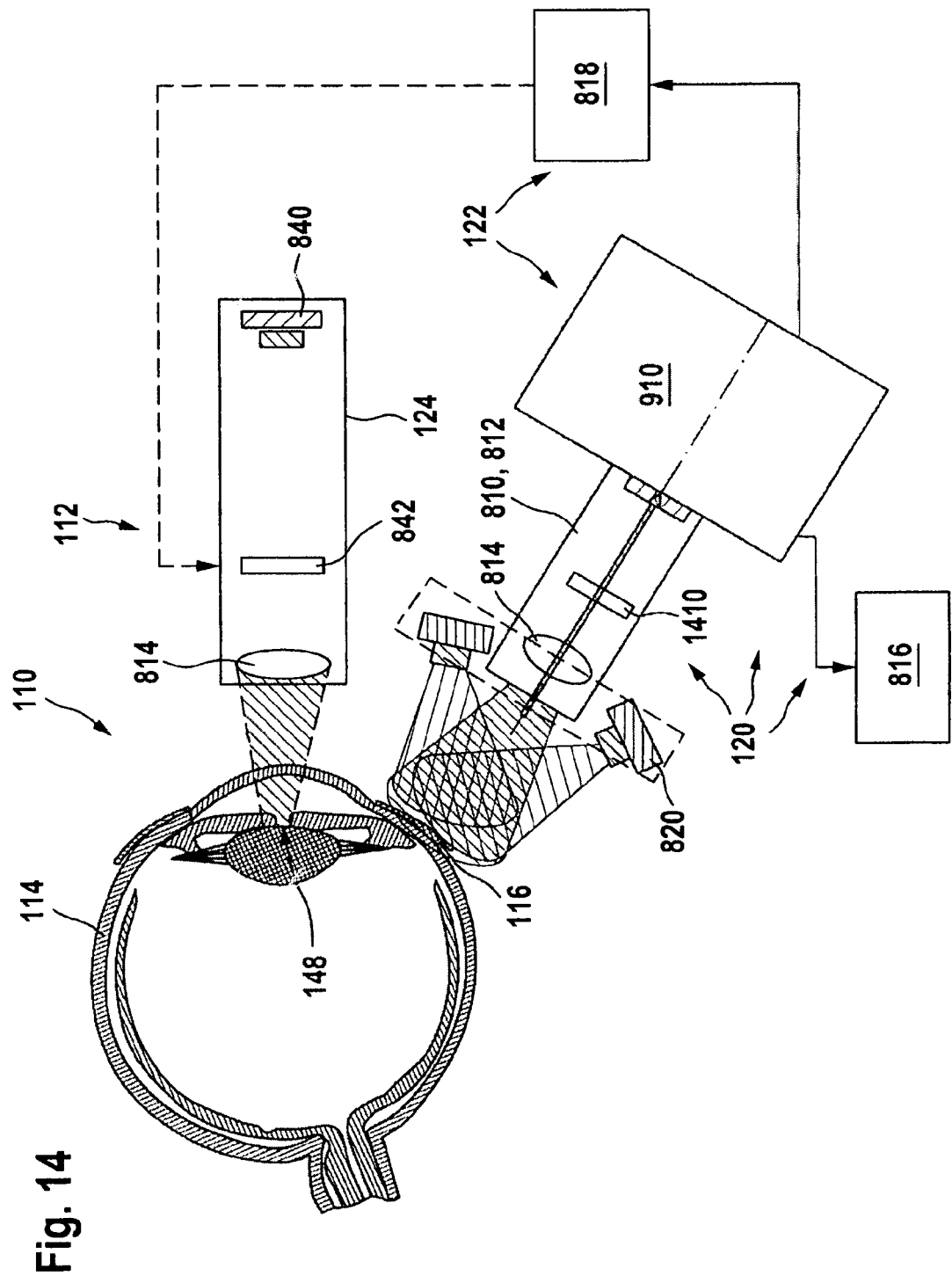

FIG. 14 shows an exemplary embodiment of an analytical measuring system 110 which has similarities to the design shown in FIG. 11. Again, a feedback unit 124 with a backlight 840 and a transparent display element 842 is provided which can be supplied with information from the positioning evaluation section 818. The positioning measurement using a camera 910 also takes place in similar fashion to the embodiment in FIG. 11.

Unlike the embodiment in FIG. 11, however, the exemplary embodiment shown in FIG. 14 is not provided with a separate donor photodiode 828. Instead, the donor fluorescent light is also evaluated using the camera 910. To isolate the donor fluorescent light and a reference fluorescent light, a filter 1410 may be provided, for example, which allows the fluorescence wavelength of the donor or of the reference fluorophor to pass sequentially, for example. Filters with spatially different transmission properties are also conceivable. This allows the intensities of the reference fluorescence and the donor fluorescence to be measured with a spatial and/or temporal resolution.

The advantage of the design shown in FIG. 14 is that the implanted ocular sensor 116 may be a very small design. A positioning for the implant is not as critical during the operation as in the case of a focusing optical system. At the same time, the measurement accuracy is less sensitive to distance than in the case of other designs. In addition, the positioning and the measurement can be performed using a single sensor, namely the camera 910, which means that component tolerances of different sensors do not need to be taken into account in relation to one another or ascertained by calibration. In addition, it is not necessary to position (for example center) the implant map on the CMOS chip of the camera 910 which acts as a sensor, since a relatively large measurement area is available.

Figure 15:
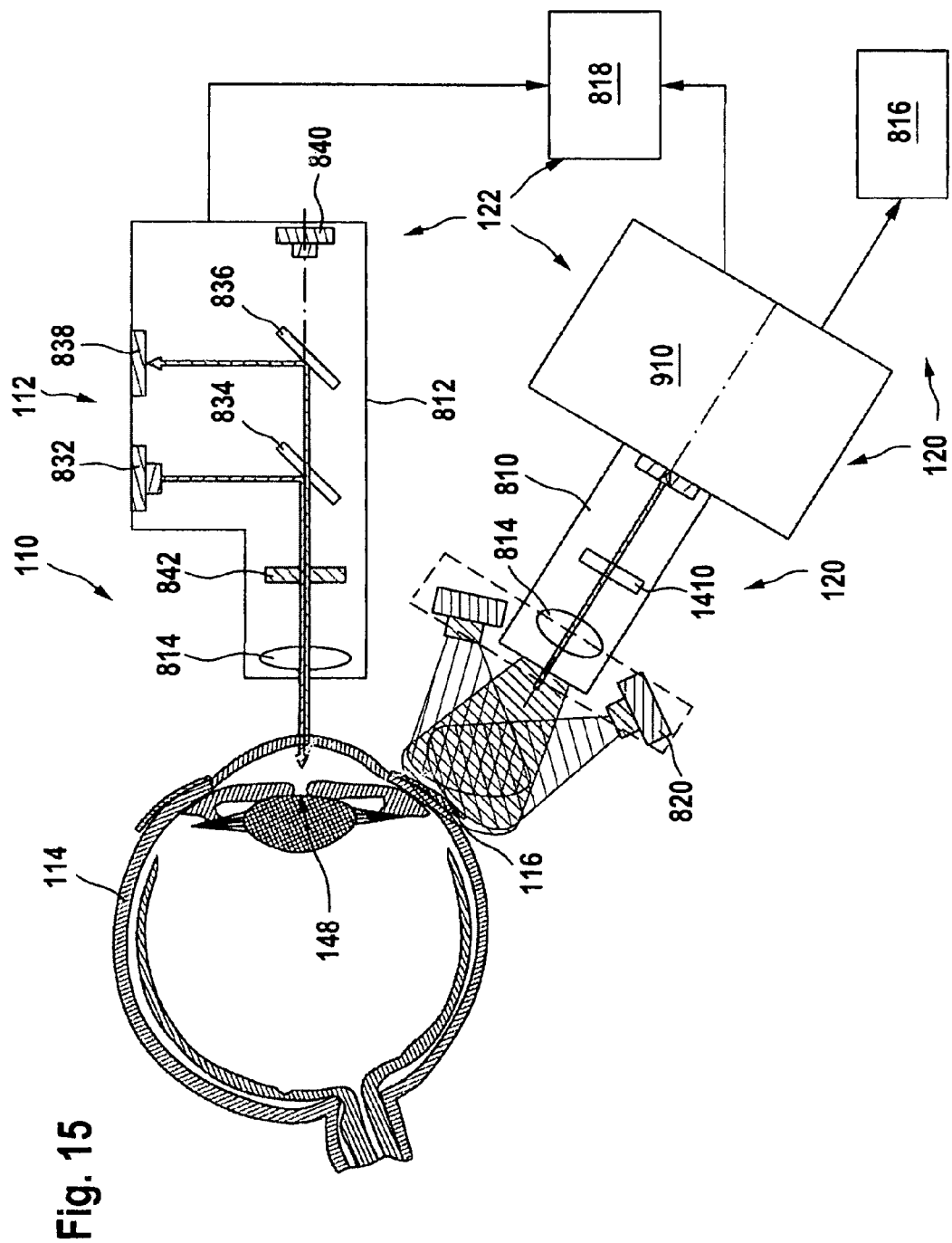

FIG. 15 shows an exemplary embodiment of the analytical measuring system 110 which combines the design of the measuring unit 810 based on the exemplary embodiment in FIG. 14 with the design of the pilot unit 812 based on the exemplary embodiment in FIG. 8. For the manner of operation and the design of these units 810, 812, reference is accordingly made to these figures.

In contrast to the design shown in FIG. 14, the analytical measuring system 110 shown in FIG. 15 allows distance measurement to be performed using the pilot unit 812 so as then to combine it by means of additional positioning information from the camera 910. Again, the transparent display element 842 can be used for feedback during the fine adjustment.

Figure 16:
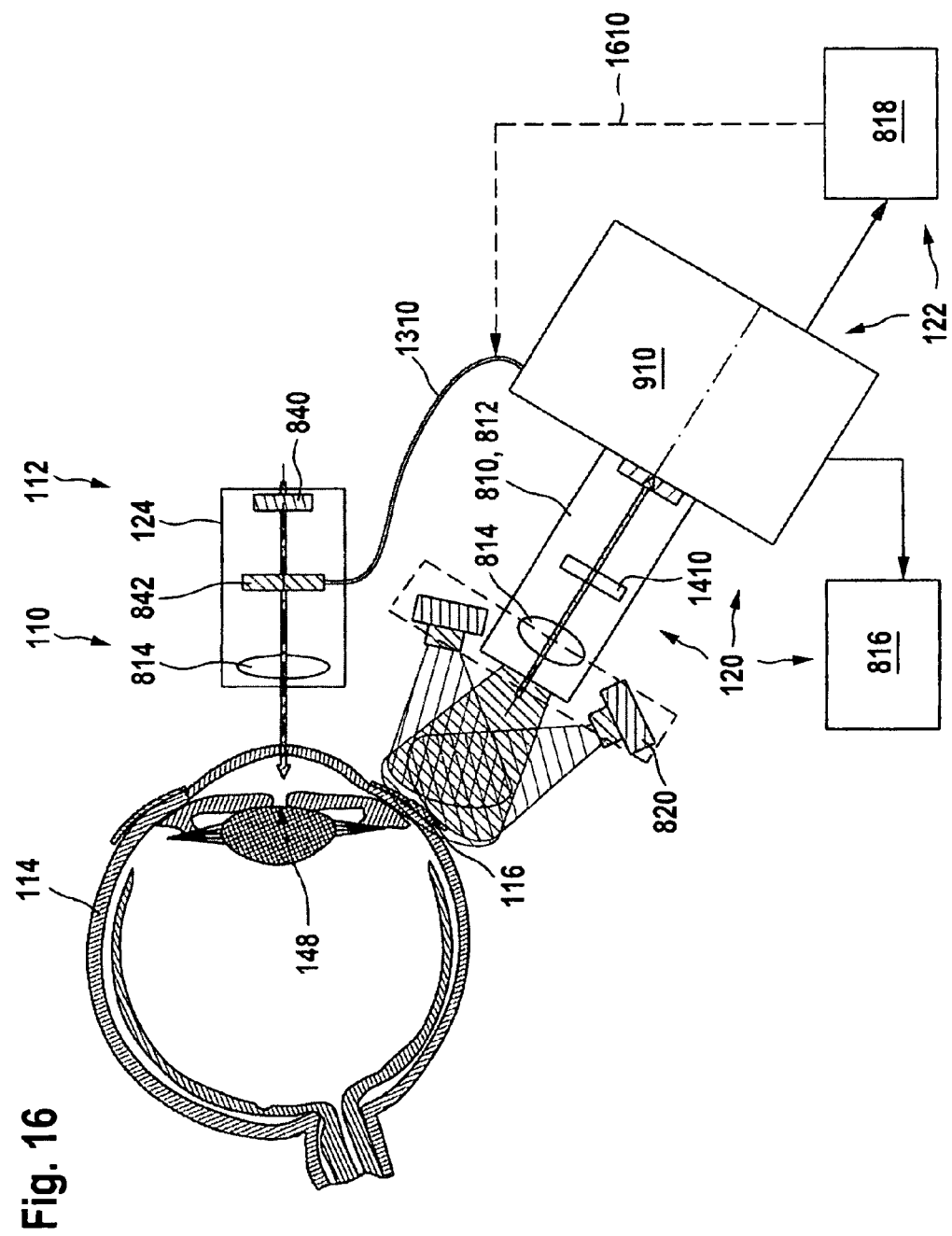

Finally, FIG. 16 shows an exemplary embodiment of the analytical measuring system 110 in which the principle of the integrated measuring unit, pilot unit 810, 812 based on the exemplary embodiment in FIGS. 14 and 15 is combined with the principle of the feedback unit 124 based on the exemplary embodiment in FIG. 13. Accordingly, an image cable 1310 is again provided between the camera 910 and the feedback unit 124 and can be used to transfer the image from the camera 910 directly onto the transparent display element 842 (for example a liquid crystal screen). This image transfer can—as indicated by the dashed arrow 1610—be controlled by the positioning evaluation section 818 or by the entire positioning system 122.

LIST OF REFERENCE SYMBOLS

110 Analytical measuring system
112 Handheld measuring appliance
114 Eye
116 Ocular sensor
118 Positioning sensor
120 Measuring system
122 Positioning system
124 Feedback unit
126 Feedback signal
128 Calibration system
130 Operator control unit
132 Optical display elements
134 Operator control elements
136 Central computation unit
138 Piezo controller
140 Drop of blood
142 Test strip
144 Measurement signals
146 Positioning signals
148 Pupil
210 Eye lens
212 Limbus
214 Conjunctiva
410 Camera
412 Body
510 First position
512 Second position
710 Magnetization
810 Measuring unit
812 Pilot unit
814 Lens
816 Measurement evaluation section
818 Positioning evaluation section
820 Excitation light emitting diode
822 Dichroic mirror
824 Dichroic mirror
826 Dichroic mirror
828 Donor photodiode
830 Reference photodiode
832 Pilot light emitting diode
834 Dichroic mirror
836 Dichroic mirror
838 Pilot photodiode
840 Backlight
842 Transparent display element
1010 Dichroic mirror
1110 Dichroic mirror
1310 Image cable
1410 Filter
1610 Control of the image transfer

The invention claimed is:

1. A handheld measuring appliance for measuring at least one analyte in an eye fluid in an eye, having
   a measuring system which is set up to measure at least one property of the at least one analyte and/or at least one analyte-dependent change of property in at least one ocular sensor in the eye fluid, and
   a positioning system which is set up to measure a three-dimensional positioning, wherein the three-dimensional positioning comprises a distance between at least one measurement location in the eye and the handheld measuring appliance and also at least one further positioning co-ordinate,
   wherein the positioning system is selected from the group consisting of: a camera system; an image recognition system; a triangulation system; a propagation time measuring system; a 1-, 2- or 3-dimensional intensity measuring system for at least one signal from a divergent electromagnetic and/or acoustic beam; and a 2- or 3-dimensional magnetoresistive measuring system.

2. The handheld measuring appliance as claimed in claim 1, wherein the measuring system is selected from the group consisting of: an infrared (IR) spectroscopic measuring system, a near infrared (NIR) spectroscopic measuring system, a RAMAN spectroscopic measuring system, a UV/visible (UV/VIS) spectroscopic measuring system, a fluorescence measuring system, an impedance measuring system, a photoacoustic measuring system, a circular dichroic measuring system, a refractometric measuring system, and an interferometric measuring system.

3. The handheld measuring appliance as claimed in claim 1, wherein the at least one further positioning co-ordinate is selected from the group consisting of: an angle of a virtual connecting line between the handheld measuring appliance and the at least one measurement location in a prescribed angle system, a co-ordinate of the handheld measuring appliance, a co-ordinate of the at least one measuring location, and an orientation angle of the handheld measuring appliance in a prescribed co-ordinate system.

4. The handheld measuring appliance as claimed in claim 1, wherein the positioning system comprises a measuring system for comparing at least two signals measured by means of two sensors in a different spatial arrangement.

5. The handheld measuring appliance as claimed in claim 1, wherein the positioning system triggers a measurement by the measuring system when at least one prescribed nominal positioning or a prescribed nominal positioning range is reached.

6. The handheld measuring appliance as claimed in claim 1, wherein the positioning system sets a spatial position and/or spatial orientation of the measuring system.

7. The handheld measuring appliance as claimed in claim 6, wherein a piezo controller is provided for setting the spatial position and/or the spatial orientation of the measuring system.

8. The handheld measuring appliance as claimed in claim 1, wherein the positioning system and/or a feedback unit of the handheld measuring appliance are set up to generate at least one feedback signal for a user on the basis of the spatial positioning.

9. The handheld measuring appliance as claimed in claim 1, wherein the handheld measuring appliance is set up to determine the concentration of the at least one analyte in the eye fluid and/or in another body fluid.

10. The handheld measuring appliance as claimed in claim 9, wherein the handheld measuring appliance is set up to take account of the spatial positioning when determining the at least one analyte concentration.

11. The handheld measuring appliance as claimed in claim 9, having additionally a calibration system, wherein the calibration system is set up to perform a comparison measurement of at least one analyte concentration in a body fluid and/or to adopt measurement data from a comparison measurement performed using a separate measuring appliance and to take them into account when determining the concentration of the at least one analyte.

12. An analytical measuring system for measuring at least one analyte in an eye fluid, comprising a handheld measuring appliance as claimed in claim 1 and also furthermore at least one ocular sensor which is suitable for being placed in contact with the eye fluid, wherein the at least one ocular sensor is designed to change at least one property upon contact with the at least one analyte, the at least one change of property being able to be measured using the measuring system.

13. The analytical measuring system as claimed in claim 12, wherein the at least one ocular sensor is selected from the group consisting of: an eye lens; and an eye implant.

14. The analytical measuring system as claimed in claim 12, wherein the at least one ocular sensor has at least one analyte receptor having at least one first fluorescence label and at least one analyte competitor having at least one second fluorescence label, wherein the at least one analyte receptor and the at least one analyte competitor are designed to change at least one property of the ocular sensor, when the at least one analyte competitor is bound to the at least one analyte receptor.

15. The analytical measuring system as claimed in claim 12, wherein the at least one ocular sensor has at least one grating and/or at least one hologram, wherein the at least one grating and/or the at least one hologram are designed to change at least one reflection property upon contact with the at least one analyte.

16. The analytical measuring system as claimed in claim 12, wherein the at least one ocular sensor furthermore has at least one reference fluorophor and/or reference colorant which is at least essentially uninfluencible by the at least one analyte.

17. The analytical measuring system as claimed in claim 12, wherein the at least one analyte is selected from the group consisting of: glucose, and a hormone.

18. The analytical measuring system as claimed in claim 12, with additionally at least one positioning sensor, wherein the at least one positioning sensor is separate from the at least one ocular sensor or is part of the at least one ocular sensor and wherein the at least one positioning sensor is designed to generate at least one signal which can be detected by the positioning system.

19. The analytical measuring system as claimed in claim 18, wherein the at least one positioning sensor is selected from the group consisting of: an eye lens; and an eye implant.

20. The analytical measuring system as claimed in claim 18, wherein the at least one signal which can be detected by the positioning system is selected from the group consisting of: a detectable shape or marker; a fluorescence; a magnetization; a reference fluorescence signal; and a reference color signal.

21. The handheld measuring appliance as claimed in claim 1, wherein the camera systems comprises a monocular or binocular camera system, having at least one camera.

22. The handheld measuring appliance as claimed in claim 1, wherein the propagation time measuring system, is for 1-, 2- or 3-dimensional propagation time measurement.

23. The handheld measuring appliance as claimed in claim 22, wherein the propagation time measuring system uses at least one laser and/or at least one phase mix detector (PMD).

24. The handheld measuring appliance as claimed in claim 9, wherein the body fluid is blood or tissue fluid.

25. The analytical measuring system as claimed in claim 13, wherein the eye lens is a contact lens.

26. The analytical measuring system as claimed in claim 19, wherein the eye lens is a contact lens.

27. The analytical measuring system as claimed in claim 14, wherein the at least one property of the ocular sensor is at least one fluorescence property.

28. A method for determining a concentration of at least one analyte in a body fluid using an analytical measuring system as claimed in claim 12, having the following steps:
    a) positioning the handheld measuring appliance coarsely in front of the eye,
    b) determining a spatial positioning,
    c) triggering a measurement by the measuring system,
    d) determining the concentration of the at least one analyte in the eye fluid from the at least one measured property of the at least one analyte and/or the at least one measured change of property of the at least one ocular sensor, and
    e) converting the concentration of the at least one analyte in the eye fluid to a concentration of the at least one analyte in the body fluid by means of a prescribed conversion algorithm.

29. A computer program with program code for carrying out method steps b), c), d) and e) of the method as claimed in claim 28 when the program is executed on a computer or computer network.

30. The computer program as claimed in claim 29, with program code which is stored on a machine-readable medium.

* * * * *